United States Patent [19]

Matsumura et al.

[11] Patent Number: 4,906,623
[45] Date of Patent: Mar. 6, 1990

[54] 3-IMIDAZOLIUM CEPHALOSPORIN DERIVATIVES

[75] Inventors: Kiyotoshi Matsumura; Hiroshi Akagi; Daisuke Suzuki; Akihiro Shimabayashi, all of Tokushima, Japan

[73] Assignee: Otsuka Kagaku Kabushiki Kaisha, Osaka, Japan

[21] Appl. No.: 172,937

[22] Filed: Mar. 25, 1988

Related U.S. Application Data

[63] Continuation of Ser. No. 902,878, Sep. 2, 1986.

[30] Foreign Application Priority Data

Sep. 3, 1985 [JP] Japan .................................. 60-194385
May 10, 1986 [JP] Japan .................................. 61-107262

[51] Int. Cl.[4] .................. A61K 31/545; C07D 501/38
[52] U.S. Cl. ...................................... 514/202; 540/222
[58] Field of Search ........................... 540/222; 514/202

[56] References Cited

U.S. PATENT DOCUMENTS 4,665,065  5/1987  Miyake ............................... 540/222
4,698,336 10/1987  Saito .................................. 514/222
4,788,185 11/1988  Miyake ............................... 540/222

FOREIGN PATENT DOCUMENTS 0062321 10/1982  European Pat. Off. ............ 540/222
0137442 10/1984  European Pat. Off. .
1038529  8/1966  United Kingdom .
2036724  7/1980  United Kingdom ................ 540/222
2037281  7/1980  United Kingdom ................ 540/222

Primary Examiner—Donald G. Daus
Attorney, Agent, or Firm—Armstrong, Nikaido, Marmelstein, Kubovcik & Murray

[57] ABSTRACT

A cephalosporin compound substituted by imidazolium ring in 3-position of cephem having the following formula (I), and pharmaceutically acceptable salt thereof,

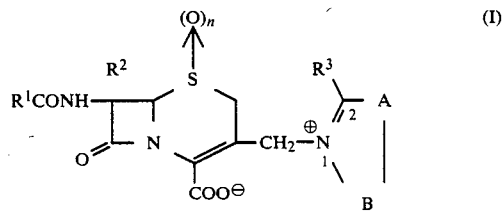

wherein $R^1$ is an organic residue known in β-lactam antibiotics, $R^2$ is hydrogen atom or methoxy, n is 0 or 1, A is a nitrogen-containing group constituting imidazolium ring, is useful as an agent for preventing and treating bacterial infections.

6 Claims, No Drawings

3-IMIDAZOLIUM CEPHALOSPORIN DERIVATIVES

This application is a continuation of Ser. No. 902,878, file Sept. 2, 1986, now abandoned.

The present invention relates to a novel cephalosporin compound substituted by imidazolium ring in C-3' position of cephem having the following formula (I) and having an anti-bacterial activity, pharmaceutically acceptable salt thereof, process thereof and pharmaceutical composition containing the derivative,

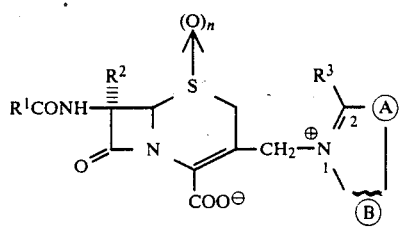

wherein $R^1$ is an organic residue known in β-lactam antibiotics, $R^2$ is hydrogen atom or methoxy, n is 0 or 1, A is the following nitrogen-containing group constituting imidazolium ring

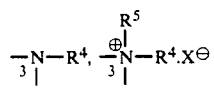

B is the following carbon-containing group constituting imidazolium ring

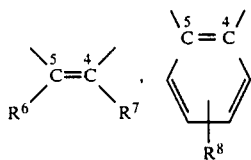

$R^3$, $R^4$, $R^5$, $R^6$, $R^7$ and $R^8$ are hydrogen atom, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_7$ cycloalkyl, substituted or unsubstituted $C_1$-$C_6$ lower alkoxyl, substituted or unsubstituted lower alkanoyl, carboxy lower alkyl, alkylcarbonylalkyl, substituted or unsubstituted phenyl, substituted or unsubstituted benzyl, lower alkylthio, carbamoyl, thiocarbamoyl, amino, amino lower alkyl, ureido, hydroxyl, halogen atom, mercapto, nitro, cyano, carboxyl, thienyl, furyl or pyridyl, $X^\ominus$ is halogen atom or acid residue.

In a cephalosporin compound having the following formula (I), and pharmaceutically acceptable salt thereof

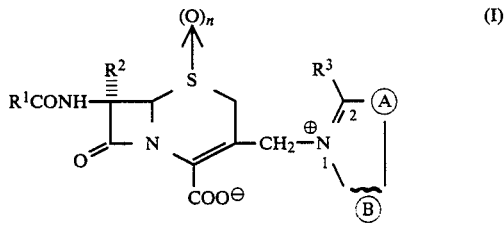

wherein $R^1$, $R^2$, $R^3$, n, A and B are same as above, there may be at least one stereoisomers such as optical isomers due to the presence of asymmetric carbon atom(s) in the molecule. The present invention includes such isomers.

Examples of useful salts of the present compound (I) are those which are pharmaceutically acceptable such as alkali metal salts (sodium salt, potassium salt, etc), alkaline earth metal salts (calcium salt, magnesium salt, etc), ammonium salt, organic amine salts (triethylamine salt, pyridinium salt, etc), inorganic acid addition salts (hydrochloride, hydrobromide, etc), organic acid addition salts (formate, trichloroacetic acid salt, methanesulfonic acid salt, etc), salts with a basic or acidic amino acid (arginine salt, aspartic acid salt, glutamic acid salt, etc).

In the present compound of the formula (I), examples of $R^1$, which are organic residue known in β-lactam antibiotics, are organic residues having 4 to 6 membered heterocyclic ring containing 1 to 4 of each of sulfur, nitrogen or oxygen atom.

Examples of such organic residues are

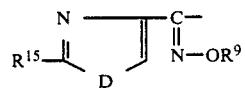

wherein D is oxygen atom or sulfur atom, $R^{15}$ is substituted or unsubstituted amino, $R^9$ is hydrogen atom; methyl, ethyl, propyl, isopropyl, butyl, isobutyl, tert-butyl and like $C_1$-$C_6$ alkyl; vinyl, propenyl, isopropenyl, butenyl, isobutenyl, pentenyl, hexenyl and like $C_2$-$C_6$ alkenyl; acetylenyl, propargyl and like $C_2$-$C_6$ alkynyl; cyclopropyl, cyclobutyl, cyclopentyl and like $C_3$-$C_7$ cycloalkyl; cyclopentenyl, cyclohexenyl and like $C_4$-$C_7$ cycloalkenyl; alkyl or alkenyl substituted by chlorine, bromine, iodine or fluorine; alkyl substituted by methylthio, ethylthio or propylthio; alkyl substituted by phenyl or benzyl; thienyl, furyl, thiazolyl and like heterocyclic ring;

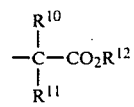

wherein $R^{10}$ and $R^{11}$ are same or different and are each hydrogen atom; methyl, ethyl, propyl, isopropyl, butyl and like $C_{1-6}$ alkyl, and preferably hydrogen atom, methyl or ethyl. $R^{12}$ is hydrogen atom; monovalent alkali metal such as sodium, potassium or lithium, preferably sodium or potassium; divalent alkaline earth metal such as calcium or magnesium; organic amine salts such as trimethylamine, triethylamine, methylamine, propylamine, N,N-dimethylethanolamine; a protective group for carboxyl such as tert-butyl, benzhydryl, 2,2,2-trichloroethyl, p-methoxybenzyl, p-nitrobenzyl, trimethylsilyl, methoxymethyl, benzyloxymethyl, diphenylmethane or phenacyl.

Other examples of organic residues represented by $R^1$ are

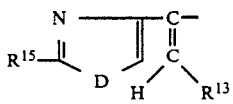

wherein D is oxygen atom or sulfur atom, $R^{15}$ is substituted or unsubstituted amino, $R^{13}$ is methyl, ethyl, propyl and like $C_{1-6}$ lower alkyl; vinyl, propenyl, isopropenyl, butenyl, isobutenyl, pentenyl, acetylenyl, propargyl and like $C_{2-6}$ lower unsaturated alkyl; cyclopropyl, cyclobutyl, cyclopentenyl and like $C_{3-7}$ cycloalkyl; nicotine, isonicotine, thienyl, furyl and like heterocyclic ring; carboxyl or esterified carboxyl; halogen atom; nitro; amino; hydroxyl; cyano; substituted or unsubstituted phenyl or benzyl;

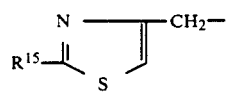

wherein $R^{15}$ is same as above,

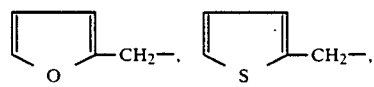

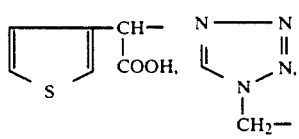

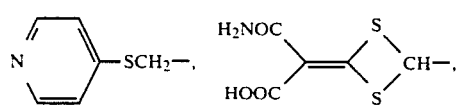

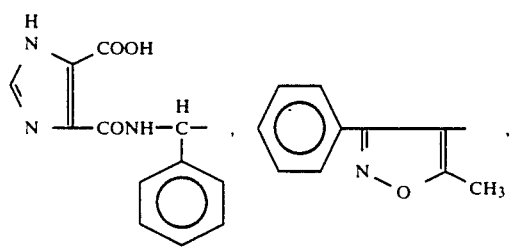

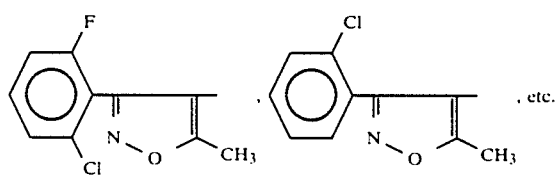

In case $R^1$ is an organic residue having substituted or unsubstituted aromatic phenyl, examples thereof are

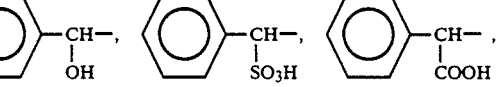

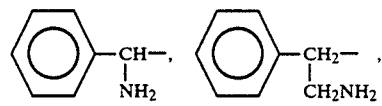

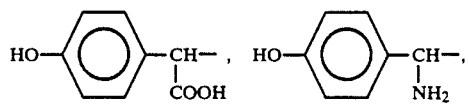

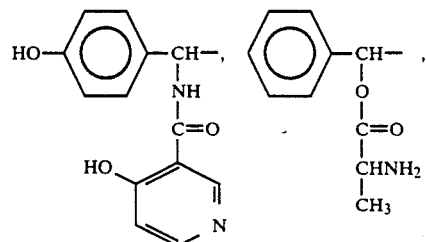

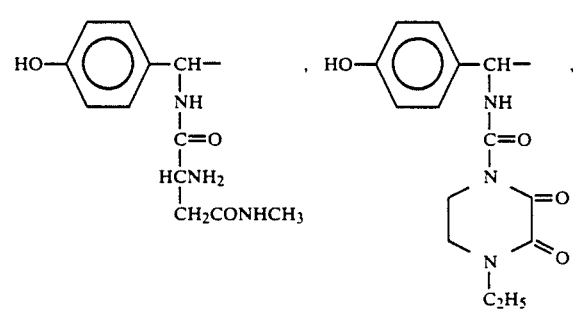

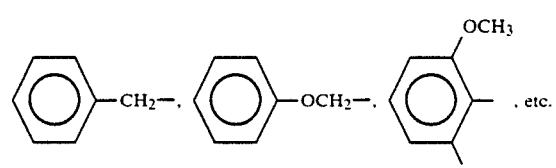

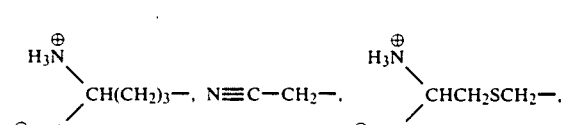

When $R^1$ is an organic residue having substituted or unsubstituted alkyl, examples thereof are

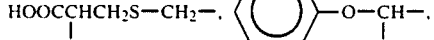

-continued

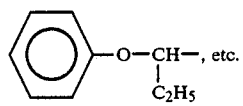

When $R^1$ is an organic residue having substituted or unsubstituted alkyl, examples thereof are

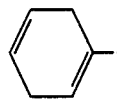  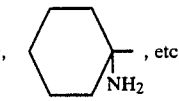

In the invention, $R^2$ is hydrogen atom or methoxy, $R^{14}$ is hydrogen atom; metal atom such as sodium, potassium, etc; ester residue; salt-forming cation; or anion charge when COO— forms intra- or inter-molecular salt with cation pair. Examples of ester residues are methyl, ethyl, propyl, isopropyl, butyl, isobutyl, tert-butyl and like $C_{1-6}$ lower alkyl; 2,2,2-trichloroethyl and like lower haloalkyl; benzyl, p-methoxybenzyl, trimethoxybenzyl, trimethoxydichlorobenzyl, p-nitrobenzyl, benzhydryl, and like substituted or unsubstituted phenylalkyl; a protective group for carboxyl such as diphenylmethyl, trityl, ditolylmethyl, phenyl-p-methoxyphenylmethyl, α-p-methoxyphenylethyl, α-p-methoxyphenyl-β-trichloroethyl, α-diphenylethyl, trimethylsilyl, benzyloxymethyl or phenacyl.

$R^3$ to $R^8$ are hydrogen atom; substituted or unsubstituted, straight-chain or branched-chain $C_1$-$C_{12}$ alkyl such as methyl, ethyl, propyl, isopropyl, butyl, isobutyl, tert-butyl, pentyl, hexyl, heptyl, octyl, nonyl, decanyl, undecanyl, dodecanyl, etc; substituted or unsubstituted, $C_2$-$C_6$ alkenyl such as vinyl, allyl, isopropenyl, butenyl, methallyl, etc; $C_2$-$C_{12}$ alkynyl such as propargyl, etc; substituted or unsubstituted, $C_3$-$C_7$ cycloalkyl such as cyclopropyl, cyclobutyl, cyclopentyl, cyclohexyl, etc; lower alkoxyl such as methoxyl, ethoxyl, propoxyl, isopropoxyl, butoxyl and like $C_1$-$C_6$ alkoxyl; substituted or unsubstituted lower alkanoyl such as formyl, acetyl, propionyl, butyryl, isobutyryl, etc; carboxy lower alkyl such as carboxymethyl, carboxyethyl, etc; alkylcarbonylalkyl such as methylcarbonylmethyl, ethylcarbonylmethyl, methylcarbonylethyl, ethylcarbonylethyl, etc; substituted or unsubstituted phenyl such as phenyl, tolyl, xylyl, hydroxyphenyl, acetylphenyl, etc; substituted or unsubstituted benzyl such as benzyl, tolylmethyl, etc; lower alkylthio such as methylthio, ethylthio, propylthio, isopropylthio, butylthio, etc; amino lower alkyl such as aminomethyl, aminoethyl, etc; halogen atom such as chlorine, bromine, fluorine, iodine, etc; carbamoyl; thiocarbamoyl; amino; ureido; hydroxyl; mercapto; nitro; cyano; carboxyl; heterocyclic ring such as thienyl, furyl, pyridyl, etc. These may have further substituent(s).

The cephalosporin compounds (I) and salts thereof of the invention can be prepared by various methods. Preferred methods are shown by the following two synthetic routes.

[Synthetic route-1]

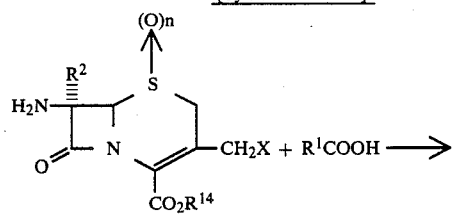

(VII)
or a reactive derivative
in amino group, or salt
thereof (VI)
or a reactive derivative
in carboxyl group, or
salt thereof

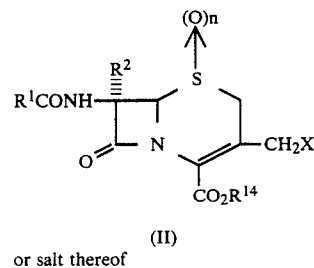

(II)
or salt thereof wherein $R^1$ and $R^2$ are same as above, $R^{14}$ is hydrogen atom, metal atom, ester residue, salt-forming cation, or anion charge when COO— forms intra- or iter-molecular salt with cation pair, n is 0 or 1, X is a group which can be replaced by a substituted or unsubstituted imidazole compound.

Compound (II) or salt thereof can be obtained by reacting Compound (VII), a reactive derivative in amino group or salt thereof and Compound (VI), a reactive derivative in carboxyl group or salt thereof. As salts of Compounds (VII) and (VI) are used the same salts enumerated with respect to Compound (I). Examples of reactive derivatives of Compound (VII) in amino group are a silyl derivative obtained from Compound (VII) and a silyl compound [e.g., bis(trimethylsilyl)acetamide, trimethylsilyl chloride, etc], a derivative obtained from Compound (VII) and an isocyanate or isothiocyanate compound, a Schiff base or its enamine-type tautomer formed by the reaction of Compound (VII) and a carbonyl compound [e.g., acetaldehyde, benzaldehyde and like aldehydes, acetone, methyl ethyl ketone and like ketones], etc.

Examples of reactive derivatives of Compound (VI) in carboxyl group are an acid chloride, acid bromide and like acid halides; an acid anhydride or symmetric acid anhydride with a substituted phosphoric acid, dialkylphosphorous acid, sulfurous acid, thiosulfuric acid, sulfuric acid, alkyl carbonate, organic carboxylic acid and like acids; an activated acid amide with an imidazole, dimethyl pyrazole, etc; an activated ester such as p-nitrophenyl ester, phenylthioester, carboxymethyl thioester, an ester with an N-hydroxypiperidine, N-hydroxysuccinimide, N-hydroxyphthalimide and like N-hydroxyl compounds; etc.

In the reaction are usable a solvent such as water, acetone, dioxane, acetonitrile, chloroform, methylene chloride, benzene, ethyl acetate, N,N-dimethylformamide, pyridine, hexane, etc, which does not affect the reaction. The solvent can be used singly or in admixture. The reaction temperature is not particularly limited and the reaction can be conducted under cooling or heating and preferably at about $-20°$ to $+40°$ C.

The reaction can be conducted in the presence of an organic or inorganic base. Examples of useful bases are lithium, sodium, potassium and like alkali metals; calcium, magnesium and like alkaline earth metals; sodium hydroxide and like alkali metal hydroxides; sodium hydride and like alkali metal hydrides; calcium hydride and like alkaline earth metal hydrides; sodium carbonate and like alkali metal carbonates; potassium hydrogen carbonate and like alkali metal hydrogen carbonates; sodium ethoxide and like alkali metal alkoxides; triethylamine and like trialkylamine; pyridine, picoline, quinoline and like nitrogen-containing heterocyclic compounds; etc. Among these bases, preferably used are trialkylamine and nitrogen-containing heterocyclic compound. The amounts of the base to be used are not particularly limited but are usually up to 25 equivalents, preferably 0.25 to 4 equivalents per equivalent of Compound (VII).

In the above reaction, the proportions of Compound (VII) and Compound (VI) to be used are not particularly limited and are selected from a wide range. However, it is preferable to use in the equivalent ratio of the former: the latter of 1:5 to 5:1, more preferably of 1:2 to 2:1.

In case Compound (VI) is used in the form of free acid or salt thereof, the reaction is conducted preferably in the presence of a condensing agent. Examples of useful condensing agents are N,N'-dicyclohexyl carbodiimide and like carbodiimide compounds; diphenyl ketene-N-cyclohexylimine and like ketene-imine compounds; ethoxyacetylene, β-chlorovinyl ethyl ether and like unsaturated alkyl ether compounds; sulfonic acid ester of N-hydroxybenzotriazole derivative [e.g., 1-(4-chlorobenzenesulfonyloxy)-6-chloro-1H-benzotriazole etc]; trialkylphosphite or triphenylphosphine with carbon tetrachloride, ethyl polyphosphate, phosphorus trichloride and like phosphorus compounds; thionyl chloride; Vilsmeyer reagent (formed from the reaction of N,N-dimethyl formamide, N-methyl formamide and like amide compound and thionyl chloride, phosphoryl chloride, phosgene and like halogen compound); etc. The above condensing agent is used usually in an amount of up to 25 equivalents, preferably 0.25 to 4 equivalents per equivalent of Compound (VII).

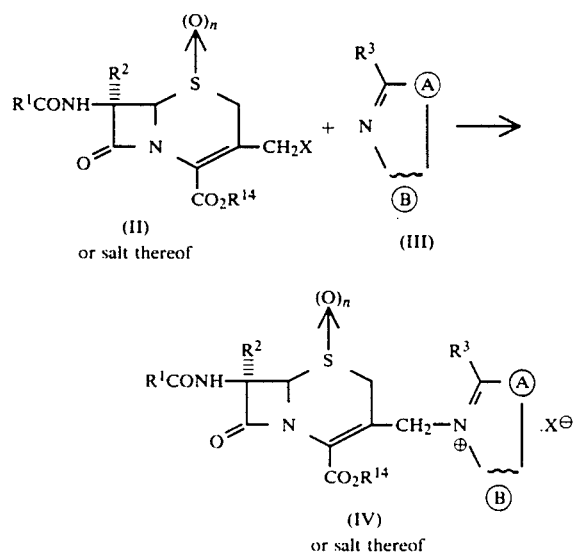

(II)
or salt thereof (III)

(IV)
or salt thereof wherein $R^1$, $R^2$, $R^3$, $R^{14}$, A, B, $X^\ominus$ and n are same as above.

The reaction of replacing C-3' position of Compound (II) by substituted or unsubstituted imidazoles (III) is preferably conducted in water or an organic solvent in the presence of a base or propylene oxide. Examples of organic solvents are acetonitrile, methanol, acetone, N,N-dimethyl formamide, tetrahydrofuran, etc. and these are used singly or in mixture thereof. The base includes sodium carbonate, sodium hydrogen carbonate, triethylamine, etc. The reaction temperature is not particularly limited but the reaction is carried out usually under cooling or heating and preferably at a temperature of about −10° to 40° C.

When $R^1$ or $R^{14}$ in Compound (IV) is amino-protecting group or carboxyl-protecting group, or when n is 1, Compound (I) is obtained by the reaction of removing amino-protecting group or carboxyl-protecting group, or by the reduction, respectively. The elimination reaction and reduction can be conducted by a usual manner such as by hydrolysis, reduction, etc. as shown below.

(A) Hydrolysis

The hydrolysis is conducted preferably in the presence of an acid. Examples of useful acids are hydrochloric acid, hydrobromic acid, sulfuric acid and like inorganic acids; formic acid, acetic acid, trifluoroacetic acid, propionic acid, benzenesulfonic acid, p-toluenesulfonic acid and like organic acids.

The hydrolysis is usually conducted in water, methanol, tetrahydrofuran, N,N-dimethyl formamide, dioxane, benzene, hexane and the like, or mixtures of such solvents, and which does not affect the reaction. In case the acid is liquid, the acid can be used as a solvent.

The reaction temperature is not particularly limited but the hydrolysis is preferably conducted under cooling or heating.

(B) Reduction

The reduction includes usual methods such as chemical reduction, catalytic reduction, etc.

Examples of chemical reducing agents are a combination of metal or metallic compound such as tin, zinc, iron, chromium chloride, chromium acetate and organic or inorganic acid such as formic acid, acetic acid, trifluoroacetic acid, p-toluenesulfonic acid, hydrochloric acid, hydrobromic acid; phosphorus tribromide; etc.

Catalysts used in the catalytic reduction include usual one containing a heavy metal such as platinum, palladium, rhodium, nickel, copper, cobalt, iron, etc.

The catalytic reduction is usually conducted in water, methanol, N,N-dimethyl formamide, hexane, benzene, dioxane and the like, or mixtures of such solvents, and which does not affect the reaction. In case the acid is liquid, the acid can be used as a solvent.

The reaction temperature is not particularly limited but the catalytic reduction is preferably conducted under cooling or heating.

[Synthetic route-2]

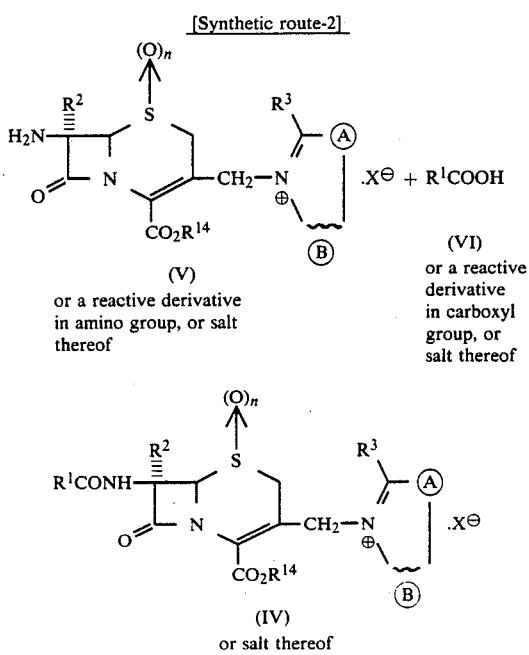

(V) or a reactive derivative in amino group, or salt thereof (VI) or a reactive derivative in carboxyl group, or salt thereof (IV) or salt thereof wherein $R^1$, $R^2$, $R^3$, $R^{14}$, A, B, $X^\ominus$ *and n are same as above.*

Compound (IV) or salt thereof can be obtained by reacting Compound (V), a reactive derivative in amino group or salt thereof and Compound (VI), a reactive derivative in carboxyl group or salt thereof. As salts of Compounds (V) and (VI) are used the same salts enumerated with respect to Compound (I). Examples of reactive derivatives of Compound (V) in amino group are same compounds which are mentioned with respect to Compound (VII) in Synthetic route-1.

As reactive derivatives of Compound (VI) in carboxyl group are enumerated the same compounds as above.

In the reaction are used the same solvents as described in the above Synthetic route-1. The reaction temperature is not particularly limited and the reaction can be conducted under cooling or heating and preferably at about −20° to +40° C.

The reaction can be conducted in the presence of an organic or inorganic base. As the bases are used the same compounds as mentioned in the above Synthetic route-1. The amounts of the base to be used are not particularly limited but are usually up to 25 equivalents, preferably 0.25 to 4 equivalents per equivalent of Compound (V).

In the above reaction, the proportions of Compound (V) and Compound (VI) to be used are not particularly limited and are selected from a wide range. However, it is preferable to use in the equivalent ratio of the former: the latter of 1:5 to 5:1, more preferably of 1:2 to 2:1.

In case Compound (VI) is used in the form of free acid or salt thereof, the reaction is conducted preferably in the presence of a condensing agent. As the condensing agents are employed the same compounds as described in the above Synthetic route-1. The above condensing agent is used usually in an amount of up to 25 equivalents, preferably 0.25 to 4 equivalents per equivalent of Compound (V).

When $R^1$ or $R^3$ in Compound (IV) is amino-protecting group or carboxyl-protecting group, or when n is 1, Compound (I) is obtained by the reaction of removing amino- or carboxyl-protecting group, or by the reduction, respectively. As the elimination reaction or reduction is conducted the same reaction as mentioned in the above Synthetic route-1.

The present Compound (I) has an excellent anti-bacterial activity and is useful for an agent for preventing and treating bacterial infections.

For preventing and treating is used a usual preparation containing, as an effective component, the present Compound (I) or a salt thereof and a pharmaceutically acceptable carrier such as an organic, inorganic, solid or liquid adjuvant suitable to oral, parenteral or local administration. The preparation may be in the form of a tablet, granule, powder, capsule and like solid form, or solution, suspension, syrup, emulsion, lemonade and like liquid form. To the preparation is added as required an auxiliary substance, stabilizer, lubricant, and other usual additives such as lactose, magnesium stearate, kaolin, sucrose, corn starch, talc, stearic acid, gelatin, agar, pectin, peanut oil, olive oil, cacao butter, ethylene glycol, etc.

The dosage of Compound (I) varies depending on age and situation of a patient, kind of disease or compound to be administered, etc. Usually, about 1 to 4000 mg or more of Compound (I) can be daily administered to a patient. For treating bacterial infections is administered Compound (I) in an average dosage per one time of about 50 mg, 100 mg, 250 mg, 500 mg, 1000 mg or 2000 mg.

The invention will be described with reference to Examples and Test Example which are not to be construed as limiting the scope of the invention. In the following, Tr is trityl group, tBu tertiary butyl group.

EXAMPLE 1

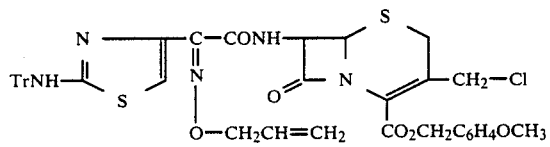

Triethylamine (0.19 ml) was added with stirring to a suspension of p-toluenesulfonic acid salt of 7-amino-3-chloromethyl-3-cephem-4-carboxylic acid p-methoxybenzyl ester (700 mg) in methylene chloride (20 ml) under a condition of ice-cooling. To the mixture was added (Z)-2-(2-allyloxyimino)-2-(2-tritylaminothiazole-4-yl) acetic acid (600 mg) and stirred to obtain a homogeneous solution. To the solution were added with stirring and under a condition of ice-cooling, 1-hydroxybenzotriazole (265 mg) and then dicyclohexylcarbodiimide (270 mg). The mixture was further stirred for 3 hours under ice-cooling. The mixture was filtered and the resulting white solid was washed with a small amount of acetone. The filtrate and washing liquid were combined and concentrated to remove a solvent at a reduced pressure. The residue was eluted through silicagel column with use of chloroform-methanol (volume ratio 8:1). The eluted solution containing a desired product was collected and concentrated to obtain 7-[2-(2-propenyloxyimino)-2-(2-tritylaminothiazole-4-yl) acetamide]-3-chloromethyl-3-cephem-4-carboxylic acid p-methoxybenzyl ester (syn-isomer) (900 mg).

NMR δ ppm (CDCl$_3$): 3.50(2H,s), 3.78(3H,s), 4.45(2H,d,J=12 Hz), 4.58(2H,d,J=5.5 Hz), 4.96(1H,d,J=5.0 Hz), 5.1–5.4(4H,m), 5.8–6.1(2H,m), 6.7(1H,s), 7.08–7.84(20H,m), 8.13(1H,s),

EXAMPLE 2

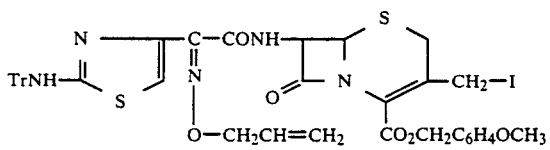

To a solution of 890 mg of 7-[2-(2-propenyloxyimino)-2-(2-tritylaminothiazole-4-yl)acetamide]-3-chloromethyl-3-cephem-4-carboxylic acid p-methoxybenzyl ester (syn-isomer) in 50 ml of acetone were added 237 mg of potassium iodide and 157 mg of sodium carbonate. The mixture was heated to reflux for one hour with stirring. The mixture was allowed to cool to room temperature and filtered. The filtrate was concentrated at a reduced pressure. The residue was dissolved in 50 ml of methylene chloride and was washed with 30 ml of 5% aqueous solution of sodium thiosulfate. The resulting organic layer was concentrated at a reduced pressure to obtain 820 mg of 7-[2-(2-propenyloxyimino)-2-(2-tritylaminothiazole-4-yl) acetamide]-3-iodomethyl-3-cephem-4-carboxylic acid p-methoxybenzyl ester (syn-isomer).

NMR δ ppm (CDCl$_3$): 3.50(2H,m), 3.82(3H,s), 4.32(2H,s), 4.70(2H,d,J=5.5 Hz), 4.90(1H,d,J=5.0 Hz), 5.1–5.4(4H,m), 5.8–6.1(2H,m), 6.7(1H,s), 7.08–7.84(20H,m), 8.13(1H,s).

EXAMPLE 3

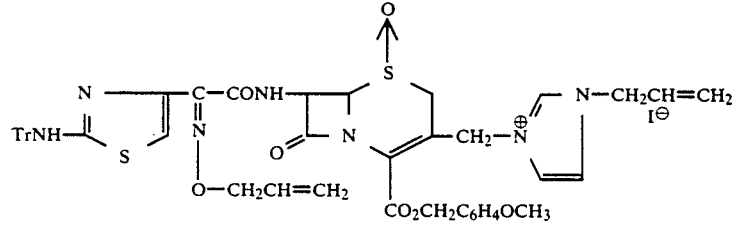

To a solution cooled at 0° C. of 5.0 g of 7-[2-(2-propenyloxyimino)-2-(2-tritylaminothiazole-4yl) acetamide]-3-iodomethyl-3-cephem-4-carboxylic acid p-methoxybenzyl ester (syn-isomer) in 160 ml of methylene chloride was added dropwise a solution of 1.5 g of m-chloroperbenzoic acid in 40 ml of methylene chloride in 10 minutes and the mixture was stirred for 50 minutes at the same temperature. The mixture was allowed to cool to room temperature and was washed with an aqueous solution of sodium carbonate, water and saturated aqueous solution of NaCl. After dehydrated with use of magnesium sulfate, the organic layer was concentrated at a reduced pressure to remove a solvent, giving 5.1 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer).

NMR δ ppm (CDCl$_3$): 3.54(2H,m,), 3.78(3H,s), 4.41(2H,m), 4.44(1H,m), 4.73(2H,m), 4.97–5.42(2H,m), 5.22(2H,s), 5.65–6.21(2H,m), 6.64(1H,s), 7.08(4H,m), 7.25(16H,s).

EXAMPLE 4

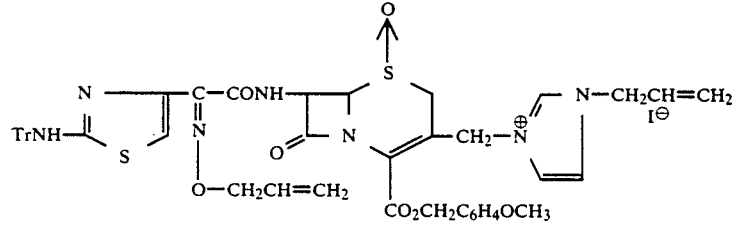

Into a mixture of THF (5 ml) and chloroform (2.5 ml) was dissolved 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer). To the solution was added with ice-cooling 64.8 mg of 1-(2-propenyl)imidazole. After the addition, the mixture was heated to room temperature and was further stirred for 3 hours. Solvents were removed at a reduced pressure. The residue was made into a powder with use of diethyl ether and purified by a silicagel column (chloroform/methanol=8/1, volume ratio) to collect eluate containing a desired compound. By removing a solvent was obtained 375.1 mg of 7-[2-(2-propenyloxyimino)-2-(2-tritylaminothiazole-4-yl) acetamide]-3-[3-(2-propenyl)-1-imidazoliomethyl]-3-cephem-1-oxido-4-carboxylic acid p-methoxybenzyl ester*iodide (syn-isomer). NMR δ ppm (DMSO-d$_6$): 3.75(2H,m), 3.80(3H,s), 4.60(2H,m), 4.88–5.47(9H,m), 5.60–6.30(3H,m), 6.81(1H,s), 7.14(4H,m), 7.32(15H,s), 7.66(2H,m), 8.74(1H,s), 8.94(1H,m), 9.06(1H,s).

EXAMPLE 5

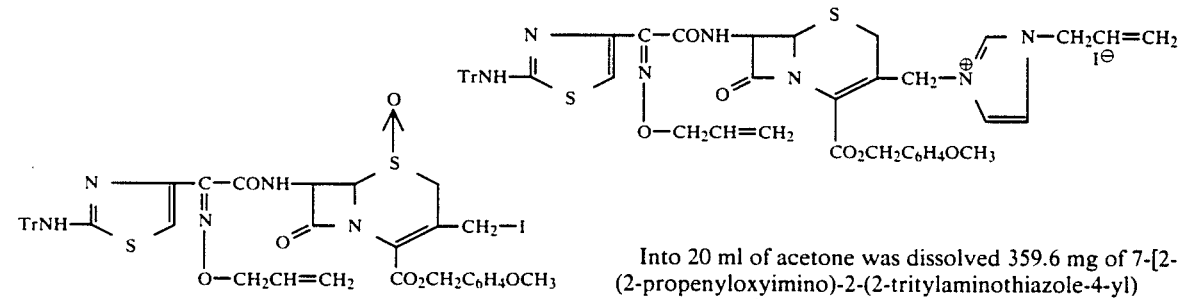

Into 20 ml of acetone was dissolved 359.6 mg of 7-[2-(2-propenyloxyimino)-2-(2-tritylaminothiazole-4-yl) acetamide]-3-[3-(2-propenyl)-1-imidazoliomethyl]-3-cephem-1-oxido-4-carboxylic acid p-methoxybenzyl ester*iodide (syn-isomer). The solution was cooled to −40° C. with dry ice-acetone refrigerant and added dropwise 270 μl of phosphorus tribromide thereto. The mixture was stirred for one hour. With cooling at the same temperature, 3 ml of aqueous solution of 500 mg of sodium carbonate was added to the mixture. After heated to room temperature, 60 ml of water was added and the mixture was extracted twice with 100 ml of ethyl acetate. The resulting organic layer was dried with anhydrous magnesium sulfate. By removing ethyl acetate was obtained 292.8 mg of 7-[2-(2-propenyloxyimino)-2-tritylaminothiazole-4-yl) acetamide]-3-[3-(2-propenyl)-1-imidazoliomethyl]-3-cephem-4-carboxylic acid p-methoxybenzyl ester*iodide (syn-isomer).

NMR δ ppm (DMSO-$d_6$): 3.50(2H,s), 3.78(3H,s), 4.56(2H,m), 4.84(2H,m), 5.01–5.60(9H,m), 5.60–6.40(3H,m), 6.72(1H,s), 7.15(4H,m), 7.31(15H,s), 7.62(2H,m), 9.05(1H,s), 9.20(1H,s), 9.53(1H,m).

EXAMPLE 6

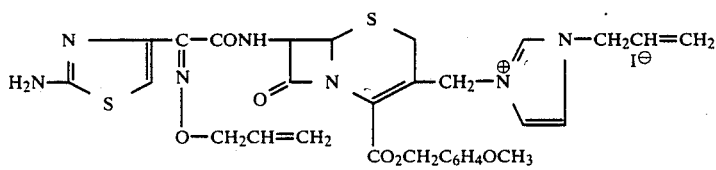

Into 3 ml of 80% aqueous solution of acetic acid was dissolved 280 mg of 7-[2-(2-propenyloxyimino)-2-(2-tritylaminothiazole-4-yl) acetamide]-3-[3-(2-propenyl)-1-imidazoliomethyl]-3-cephem-4-carboxylic acid p-methoxybenzyl ester*iodide (syn-isomer). The solution was stirred at 35° to 40° C. for 2 hours and the solvent was removed by freeze-drying. To the residue was added diethyl ether and powder separated was collected by filtration to obtain 209.2 mg of 7-[2-(2-aminothiazole-4-yl)-2-(2-propenyloxyimino) acetamide]-3-[3-(2-propenyl)-1-imidazoliomethyl]-3cephem-4-carboxylic acid p-methoxybenzyl ester*iodide (syn-isomer).

NMR δ ppm (DMSO-$d_6$): 3.54(2H,s), 3.76(3H,s), 4.58(2H,m), 4.83(2H,m), 5.0–5.54(9H,m), 5.61–6.35(3H,m), 6.78(1H,s), 6.83(2H,s), 7.13(4H,m), 7.68(2H,m), 9.22(1H,s), 9.63(1H,s).

EXAMPLE 7

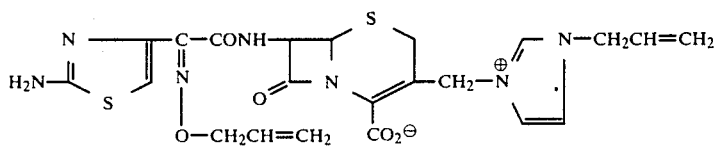

In a mixture of methylene chloride (3 ml), trifluoroacetic acid (930 μl) and anisole (650 μl) was added 190 mg of 7-[2-(2-aminothiazole-4yl)-2-(2-propenyloxyimino) acetamide]-3-[3-(2-propenyl)-1-imidazoliomethyl]-3-cephem-4-carboxylic acid p-methoxybenzyl ester*iodide (syn-isomer). The mixture was stirred at ice-cooling for 2 hours. The solvent was removed at a reduced pressure. To the residue was added 100 ml of diethyl ether to separate out powder. The powder was collected by filtration, neutralized with an aqueous solution of potassium hydrogen carbonate and freeze-dried to obtain yellow crude powder. The powder was subjected to Sephadex LH-20 column (methanol) to obtain an eluate containing a desired compound. By removing a solvent at a reduced pressure was obtained 68.4 mg of 7-[2-(2-aminothiazole-4-yl)-2-(2-propenyloxyimino) acetamide]-3-[3-(2-propenyl)-1-imidazoliomethyl]-3-cephem-4-carboxylate.

NMR δ ppm (DMSO-$d_6$): 3.65(2H,m), 4.57(2H,m), 4.82(2H,m), 5.01–5.5(7H,m), 5.55–6.35(3H,m), 6.83(1H,s), 7.17(2H,s), 7.63(2H,m), 9.23(1H,s), 9.35(1H,d,J=8.0 Hz).

EXAMPLE 8

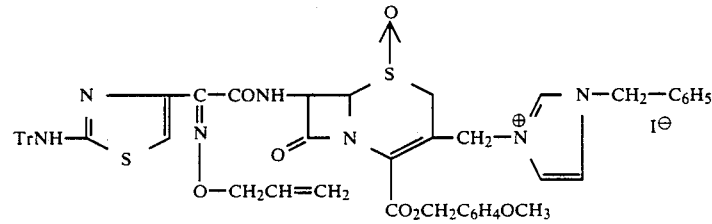

In the same manner as in Example 4, from 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 94.8 mg of 1-benzylimidazole was obtained 418.3 mg of 7-[2-(2-propenyloxyimino)-2-(2-tritylaminothiazole-4-yl) acetamide]-3-(3-benzyl-1-imidazoliomethyl)-3-cephem-1-oxido-4-carboxylic acid p-methoxybenzyl ester*iodide (syn-isomer).

NMR δ ppm (DMSO-$d_6$): 3.65(2H,m), 3.28(3H,s), 4.56(2H,m), 4.97(1H,m), 5.01–5.60(8H,m), 5.51–6.30(2H,m), 6.80(1H,s), 7.12(4H,m), 7.32(15H,s), 7.43(5H,s), 7.62(2H,s), 7.73(1H,s), 8.73(1H,s), 8.91(1H,m), 9.40(1H,s).

EXAMPLE 9

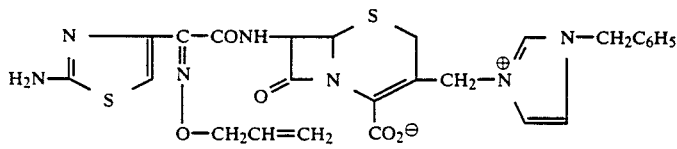

In the same manner as in Examples 5, 6 and 7, from 408.3 mg of 7-[2-(2-propenyloxyimino)-2-(2-tritylaminothiazole-4-yl) acetamide]-3-(3-benzyl-1imidazoliomethyl)-3-cephem-1-oxido-4-carboxylic acid p-methoxybenzyl ester*iodide (syn-isomer) was obtained 37.2 mg of 7-[2-(2-aminothiazole-4-yl)-2-(2-propenyloxyimino) acetamide]-3-(3-benzyl-1-imidazoliomethyl)-3-cephem-4-carboxylate (syn-isomer).

NMR δ ppm (DMSO-d$_6$): 3.47(2H,m), 4.68(2H,m), 4.80–5.50(5H,m), 5.41(2H,s), 5.60–6.23(2H,m), 6.93(1H,s), 7.37(5H,s), 7.67(2H,m), 9.23(1H,s).

EXAMPLE 10

In the same manner as in Examples 5, 6 and 7, from 425.9 mg of 7-[2-(2-propenyloxyimino)-2-(2-tritylaminothiazole-4-yl) acetamide]-3-(3-tert-butoxycarbomethyl-1-imidazoliomethyl)-3-cephem-1-oxido-4-carboxylic acid p-methoxybenzyl ester*iodide (syn-isomer) was obtained 50.3 mg of 7-[2-(2-aminothiazole-4-yl)-2-(2-propenyloxyimino) acetamide]-3-[3-(potassium acetate)-1-imidazoliomethyl]-3-cephem-4-carboxylate (syn-isomer).

NMR δ ppm (DMSO-d$_6$): 3.50(2H,m), 4.70(2H,m), 4.95–5.61(7H,m), 5.67–6.41(2H,m), 6.98(1H,s), 7.74(2H,s), 9.21(1H,s).

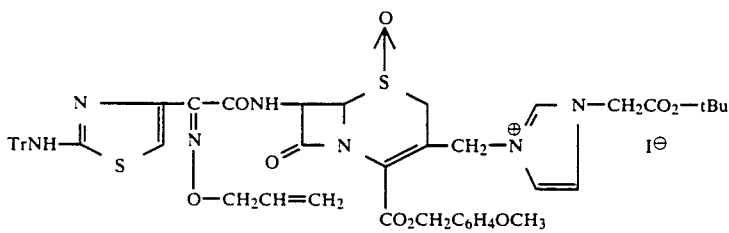

In the same manner as in Example 4, from 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 109.2 mg of 1-tert-butoxycarbomethylimidazole was obtained 447.4 mg of 7-[2-(2-propenyloxyimino)-2-(2-tritylaminothiazole-4-yl) acetamide]-3-(3-tert-butoxycarbomethyl-1-imidazoliomethyl)-3-cephem-1-oxido-4-carboxylic acid p-methoxybenzyl ester*iodide (syn-isomer).

NMR δ ppm (DMSO-d$_6$): 2.97(9H,s), 3.63(2H,m), 3.78(3H,s), 4.07(2H,m), 4.86(2H,s), 4.91–5.54(7H,m), 5.70–6.35(2H,m), 6.81(1H,s), 7.17(4H,m), 7.37(15H,s), 7.22(2H,m), 8.74(1H,s), 8.83(1H,m), 9.12(1H,s).

EXAMPLE 11

EXAMPLE 12

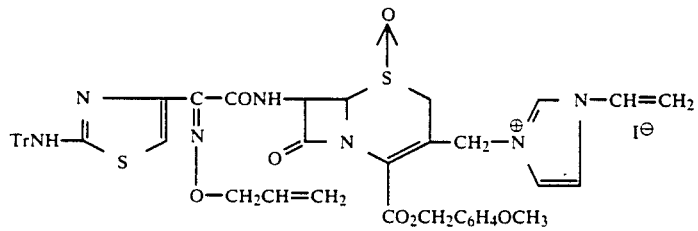

In the same manner as in Example 4, from 0.5 g of 7-[2-(2-propenyloxyimino)-2-(2-trityl-aminothiazole-4-yl) acetamide]-3-iodomethyl-3-cephem-1-oxido-4-carboxylic acid p-methoxybenzyl ester (syn-isomer) and 57 μl of 1-vinylimidazole was obtained 380 mg of 7-[2-(2-propenyloxyimino)-2-(2-trityl-aminothiazole-4-yl) acetamide]-3-(3-vinyl-1-imidazoliomethyl)-3-cephem-1-oxido-4-carboxylic acid p-methoxybenzyl ester*iodide (syn-isomer).

NMR δ PPM (DMSO-d$_6$): 3.75(2H,m), 3.80(3H,s), 4.60(2H,m), 4.85–5.47(9H,m), 7.32(15H,s), 7.66(2H,m), 8.74(1H,s), 8.94(1H,m), 9.06(1H,s).

EXAMPLE 13

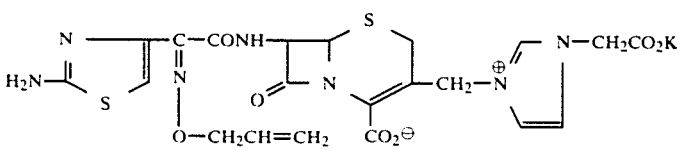

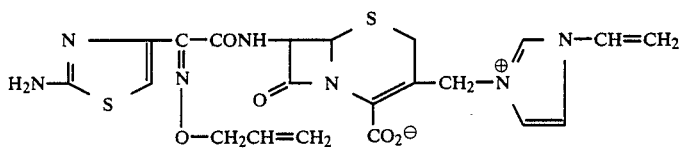

In the same manner as in Examples 5, 6 and 7, from 350 mg of 7-[2-(2-propenyloxyimino)-2-(2-tritylaminothiazole-4-yl) acetamide]-3-(3-vinyl-1-imidazoliomethyl)-3-cephem-1-oxido-4-carboxylic acid p-methoxybenzyl ester*iodide (syn-isomer) was obtained 29 mg of 7-[2-(2-aminothiazole-4-yl)-2-(2-propenyloxyimino) acetamide]-3-(3-vinyl-1-imidazoliomethyl) -3-cephem-4-carboxylate (syn-isomer).

NMR δ ppm (DMSO-$d_6$): 3.75(2H,m), 4.60(2H,m), 4.80–5.47(9H,m), 6.78(1H,s), 6.83(2H,s), 7.17(2H,s), 9.23(1H,s), 9.35(1H,d,J=8.0 Hz).

EXAMPLE 14

In the same manner as in Examples 5, 6 and 7, from 310 mg of 7-[2-(2-propenyloxyimino)-2-(2-tritylaminothiazole-4-yl) acetamide]-3-(3-acetophenyl-1-imidazoliomethyl)-3cephem-1-oxido-4-carboxylic acid p-methoxybenzyl ester*iodide (syn-isomer) was obtained 53 mg of 7-[2-(2-aminothiazole-4-yl)-2-(2-propenyloxyimino) acetamide]-3-(3-acetophenyl-1-imidazoliomethyl)-3-cephem-4-carboxylate.

NMR δ ppm (DMSO-$d_6$): 3.75(2H,m), 4.50(2H,m), 5.0(2H,m), 5.50(1H,m), 6.65(1H,s), 7.0(2H,s), 9.06(1H,d,J=8.0 Hz).

EXAMPLE 16

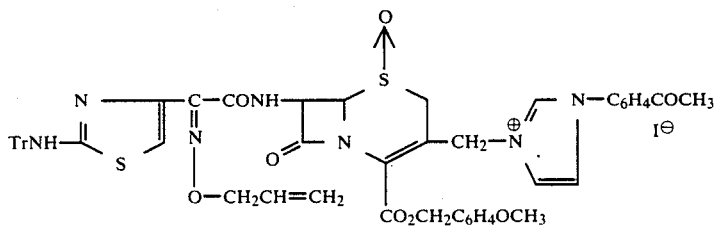

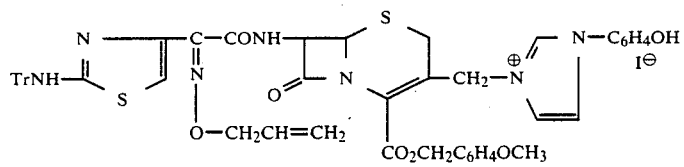

In the same manner as in Example 4, from 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 100 μl of 4-imidazole acetophenone was obtained 330 mg of 7-[2-(2-propenyloxyimino)-2-(2-tritylaminothiazole-4-yl) acetamide]-3-(3-acetophenyl-1-imidazoliomethyl)-3-cephem-1-oxido-4-carboxylic acid p-methoxybenzyl ester*iodide (syn-isomer).

NMR δ ppm (DMSO-$d_6$): 3.80(3H,s), 3.75(2H,m), 4.50(2H,m), 4.56(2H,m), 5.0(2H,m), 5.15(4H,m), 6.60(1H,s), 7.32(18H,m), 9.30(1H,d,J=8.0 Hz).

EXAMPLE 15

In the same manner as in Example 4, from 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 88 μof 4-imidazole acetophenone was obtained 310 mg of 7-[2-(2-propenyloxyimino)-2-(2-tritylaminothiazole-4-yl)acetamide]-3-[3-(4-hydroxyphenyl)-1-imidazoliomethyl]-3-cephem-1-oxido-4-carboxylic acid p-methoxybenzyl ester*iodide (syn-isomer).

NMR δ ppm (DMSO-$d_6$): 3.80(3H,s), 3.75(2H,m), 4.50(2H,m), 4.56(2H,m), 5.75–6.10(4H,m), 7.0–7.32(17H,m), 9.20(1H,d,J=8.0 Hz).

EXAMPLE 17

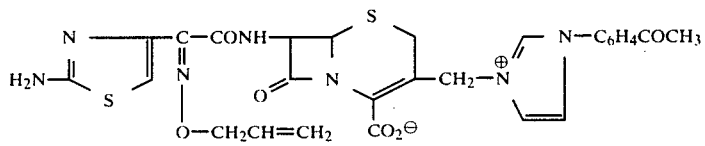

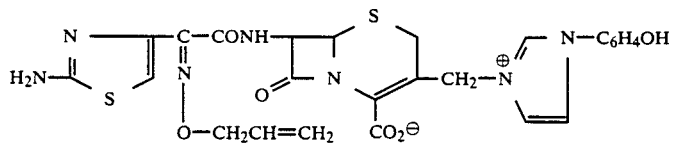

In the same manner as in Examples 5, 6 and 7, from 290 mg of 7-[2-(2-propenyloxyimino)-2-(2-tritylaminothiazole-4-yl) acetamide]-3-[3-(4-hydroxyphenyl)-1-imidazoliomethyl]-3-cephem-1-oxido-4-carboxylic acid p-methoxybenzyl ester*iodide (syn-isomer) was obtained 53 mg of 7-[2-(2-aminothiazole-4-yl)-2-(2-propenyloxyimino) acetamide]-3-[3-(4-hydroxyphenyl)-1-imidazoliomethyl]-3-cephem-4-carboxylate (syn-isomer).

NMR δ ppm (DMSO-d6): 3.75(2H,m), 4.50(2H,m), 4.56(2H,m), 5.75–6.10(4H,m), 7.2(6H,m), 9.20(1H,d,J=8.0 Hz).

In the same manner as in Examples 5, 6 and 7, from 315 mg of 7-[2-(2-propenyloxyimino)-2-(2-tritylaminothiazole-4-yl) acetamide]-3-[3-(2-propynyl)-1-imidazoliomethyl]-3-cephem-1-oxido-4-carboxylic acid p-methoxybenzyl ester*iodide (syn-isomer) was obtained 38 mg of 7-[2-(2-aminothiazole-4-yl)-2-(2-propenyloxyimino) acetamide]-3-[3-(2-propynyl)-1-imidazoliomethyl]-3-cephem-4-carboxylate.

NMR δ ppm (DMSO-d6): 3.9–4.4(2H,m), 4.6(2H,s), 4.85(1H,d,J=5.0 Hz), 5.45(1H,m), 6.72(1H,s), 7.10(2H,s), 9.45(1H,d,J=8.0 Hz).

EXAMPLE 20

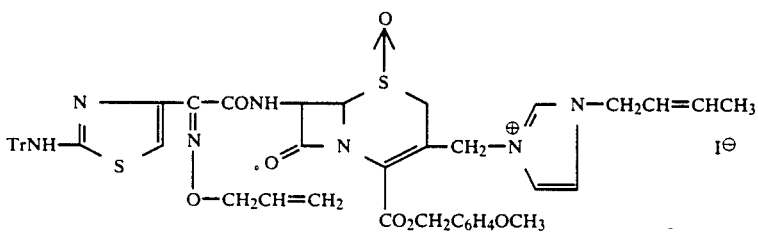

EXAMPLE 18

In the same manner as in Example 4, from 0.5 g of

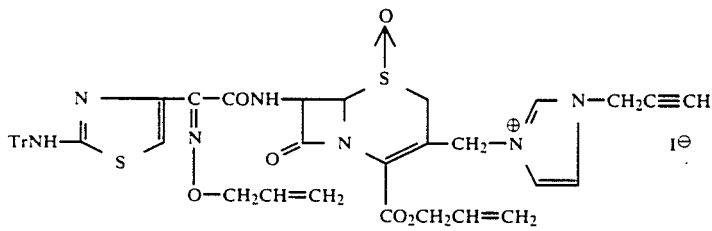

In the same manner as in Example 4, from 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 58 μl of 1-propynylimidazole was obtained 325 mg of 7-[2-(2-propenyloxyimino)-2-(2-tritylaminothiazole-4-yl) acetamide]-3-[3-(2-propynyl)-1-imidazoliomethyl]-3-cephem-1-oxido-4-carboxylic acid p-methoxybenzyl ester*iodide (syn-isomer).

NMR δ (DMSO-d6): 3.9–4.4(2H,m), 4.6(2H,s), 4.85(1H,d,J=5.0 Hz), 5.45(1H,m), 6.72(1H,s), 7.25(15H,s), 9.45(1H,d,J=8.0 Hz).

EXAMPLE 19

7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 68 μl of 1-(2-butenyl)imidazole was obtained 365 mg of 7-[2-(2-propenyloxyimino)-2-(2-tritylaminothiazole-4-yl) acetamide]-3-[3-(2-butenyl)-1-imidazoliomethyl]-3-cephem-1oxido-4-carboxylic acid p-methoxybenzyl ester*iodide (syn-isomer).

NMR δ ppm (DMSO-d6): 1.7(3H,d,J=6.0), 3.9–4.4(2H,m), 4.6(2H,s), 4.85(1H,d,J=5.0 Hz), 5.45(1H,m), 6.72(1H,s), 7.25(15H,s), 9.45(1H,d,J=8.0 Hz).

EXAMPLE 21

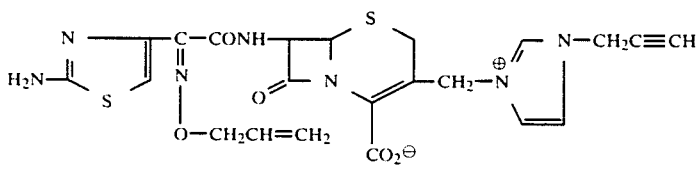

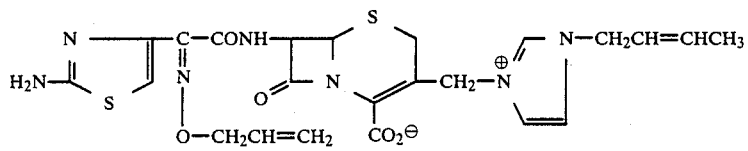

In the same manner as in Examples 5, 6 and 7, from 353 mg of 7-[2-(2-propenyloxyimino)-2-(2-tritylaminothiazole-4-yl) acetamide]-3-[3-(2-butenyl)-1-imidazoliomethyl]-3-cephem-1-oxido-4-carboxylic acid p-methoxybenzyl ester*iodide was obtained 57 mg of 7-[2-(2-aminothiazole-4-yl)-2-(2-propenyloxyimino) acetamide]-3-[3-(2-butenyl)-1-imidazoliomethyl]-3-cephem-4-carboxylate (syn-isomer). NMR δ ppm (DMSO-$d_6$): 1.7(3H,d,J=6.0), 3.9–4.4(2H,m), 4.6(2H,s), 4.85(1H,d,J=5.0 Hz), 5.45(1H,m), 6.73(1H,s), 7.10(2H,s), 9.45(1H,d,J=8.0 Hz).

EXAMPLE 22

In the same manner as in Examples 5, 6 and 7, from 348 mg of 7-[2-(2-propenyloxyimino)-2-(2-tritylaminothiazole-4-yl) acetamide]-3-[3-(3-butenyl)-1-imidazoliomethyl]-3-cephem-1-oxido-4-carboxylic acid p-methoxybenzyl ester*iodide (syn-isomer) was obtained 51 mg of 7-[2-(2-aminothiazole-4-yl)-2-(2-propenyloxyimino) acetamide]-3-[3-(3-butenyl)-1-imidazoliomethyl]-3-cephem-4-carboxylate (syn-isomer).

NMR δ ppm (DMSO-$d_6$): 2.28(2H,m), 3.85(2H,m), 4.6(2H,s), 4.85(1H,d,J=5.0 Hz), 5.45(1H,m), 6.76(1H,s), 7.01(2H,s), 9.20(1H,d,J=8.0 Hz).

EXAMPLE 24

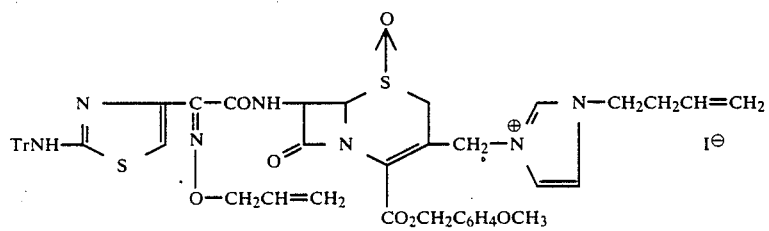

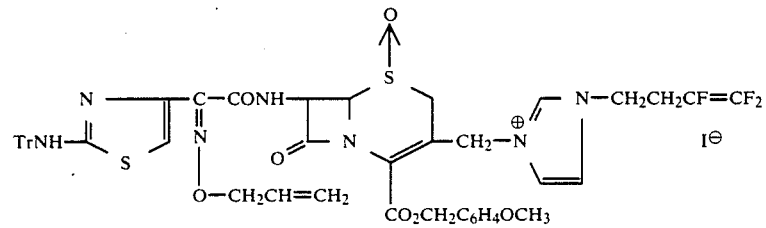

In the same manner as in Example 4, from 0.5 g of 7-[2-(2-propenyloxyimino)-2-(2-tritylaminothiazole-4-yl) acetamide]-3-iodomethyl-3-cephem-4-carboxylic acid p-methoxybenzyl ester (syn-isomer) and 68 μl of 1-(3-butenyl)imidazole was obtained 353 mg of 7-[2-(2-propenyloxyimino)-2-(2-tritylaminothiazole-4-yl) acetamide]-3-[3-(3-butenyl)-1-imidazoliomethyl]-3-cephem-1-oxido-4-carboxylic acid p-methoxy benzyl ester*iodide (syn-isomer).

NMR δ ppm (DMSO-$d_6$): 2.28(2H,m), 3.85(2H,m), 4.6(2H,s), 4.85(1H,d,J=5.0 Hz), 5.45(1H,m), 6.76(1H,s), 7.25(15H,s), 9.20(1H,d,J=8.0 Hz).

EXAMPLE 23

In the same manner as in Example 4, from 0.5 g of 7-[2-(2-propenyloxyimino)-2-(2-tritylaminothiazole-4-yl)acetamide]-3-iodomethyl-3-cephem-4-carboxylic acid p-methoxybenzyl ester (syn-isomer) and 100 μl of 1-(3,4,4-trifluoro-3-butenyl)imidazole was obtained 213 mg of 7-[2-(2-propenyloxyimino)-2-(2-tritylaminothiazole-4-yl) acetamide]-3-[3-(3,4,4-trifluoro-3-butenyl)-1-imidazoliomethyl]-3-cephem-1-oxido-4-carboxylic acid p-methoxybenzyl ester*iodide (syn-isomer).

NMR δ ppm (DMSO-$d_6$): 2.7–3.0(2H,m), 4.0(2H,m), 4.6(2H,s), 4.85(1H,d,J=5.0 Hz), 5.45(1H,m), 6.70(1H,s), 7.30(15H,s), 9.30(1H,d,J=8.0 Hz).

EXAMPLE 25

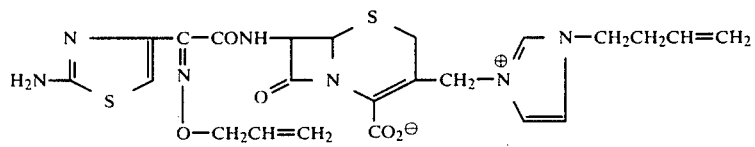

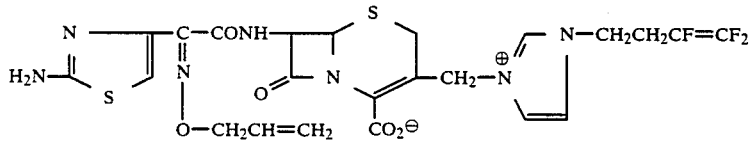

In the same manner as in Examples 5, 6 and 7, from 200 mg of 7-[2-(2-propenyloxyimino)-2-(2-tritylaminothiazole-4-yl) acetamide]-3-[3-(3,4,4-trifluoro-3-butenyl)-1-imidazoliomethyl]-3-cephem-1-oxido-4-carboxylic acid p-methoxybenzyl ester*iodide (syn-isomer) was obtained 21 mg of 7-[2-(2-aminothiazole-4-yl)-2-(2-propenyloxyimino) acetamide]-3-[3-(3,4,4-trifluoro-3-butenyl)-1-imidazoliomethyl]-3-cephem-4-carboxylate (syn-isomer).

NMR δ ppm (DMSO-d6): 2.7–3.0(2H,m), 4.0(2H,m), 4.6(2H,s), 4.85(1H,d,J=5.0 Hz), 5.45(1H,m), 6.70(1H,s), 7.10(2H,s), 9.32(1H,d,J=8.0 Hz).

In the same manner as in Examples 5, 6 and 7, from 300 mg of 7-[2-(2-propenyloxyimino)-2-(2-tritylaminothiazole-4-yl) acetamide]-3-(3-methyl-1-imidazoliomethyl)-3-cephem-1-oxido-4-carboxylic acid p-methoxybenzyl ester*iodide (syn-isomer) was obtained 25.1 mg of 7-[2-(2-aminothiazole-4-yl)-2-(2-propenyloxyimino) acetamide]-3-(3-methyl-1-imidazoliomethyl)-3-cephem-4-carboxylate (syn-isomer).

NMR δ ppm (DMSO-d6): 3.48(2H,m), 3.85(3H,s), 4.17(2H,s), 4.90–5.50(5H,m), 5.86(1H,m), 5.70–6.40(1H,m), 7.65(2H,s), 9.10(1H,s).

EXAMPLE 28

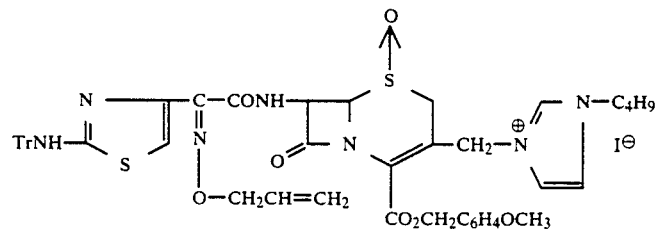

In the same manner as in Example 4, from 0.5 g of

EXAMPLE 26

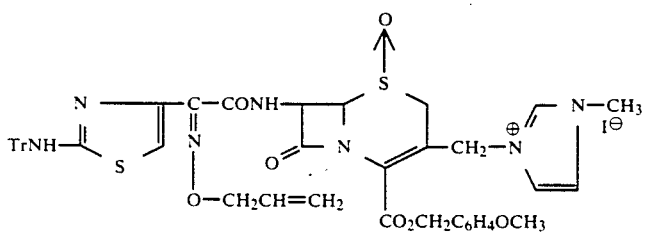

In the same manner as in Example 4, from 0.5 g of 7-[2-(2-propenyloxyimino)-2-(2-tritylaminothiazole-4-yl) acetamide]-3-iodomethyl-3-cephem-4-carboxylic acid p-methoxybenzyl ester (syn-isomer) and 50 μl of 1-methylimidazole was obtained 336 mg of 7-[2-(2-propenyloxyimino)-2-(2-tritylaminothiazole-4-yl) acetamide]-3-(3-methyl-1-imidazoliomethyl)-3-cephem-1-oxido-4-carboxylic acid p-methoxybenzyl ester*iodide (syn-isomer).

NMR δ ppm (DMSO-d6): 3.65(2H,m), 3.73(3H,s), 3.85(3H,s), 4.64(2H,m), 4.97(1H,m), 5.0–5.50(6H,m), 5.6–6.40(2H,m), 6.92(1H,s), 7.07(4H,m), 7.31(15H,s), 7.60(2H,m), 8.80(1H,s).

EXAMPLE 27

7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 63 μl of 1-butylimidazole was obtained 310 mg of 7-[2-(2-propenyloxyimino)-2-(2-tritylaminothiazole-4-yl)-acetamide]-3-(3-butyl-1-imidazoliomethyl)-3-cephem-1-oxido-4-carboxylic acid p-methoxybenzyl ester*iodide (syn-isomer).

NMR δ ppm (DMSO-d6): 1.40(9H,s), 1.6–2.11(4H,m), 3.68(3H,s), 4.8(2H,m), 5.1–5.6(4H,m), 5.80(1H,m), 6.68(1H,s), 7.25(15H,s), 9.4(1H,d,J=8.0 Hz).

EXAMPLE 29

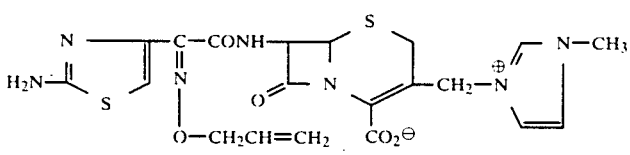

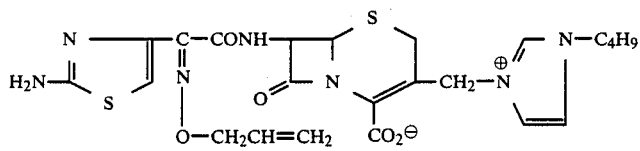

In the same manner as in Examples 5, 6 and 7, from 300 mg of 7-[2-(2-propenyloxyimino)-2-(2-tritylaminothiazole-4-yl) acetamide]-3-(3-butyl-1imidazoliomethyl)-3-cephem-1-oxido-4-carboxylic acid p-methoxybenzyl ester*iodide (syn-isomer) was obtained 21 mg of 7-[2-(2-aminothiazole-4-yl)-2-(2-propenyloxyimino) acetamide]-3-(3-butyl-1-imidazoliomethyl)-3-cephem-4-carboxylate.

NMR δ ppm (DMSO-$d_6$): 1.40(9H,s), 1.6–2.11(4H,m), 3.68(3H,s), 4.8(2H,m), 5.1–5.6(4H,m), 5.80(1H,m), 6.68(1H,s), 7.10(2H,s), 9.4(1H,d,J=8.0 Hz).

In the same manner as in Examples 5, 6 and 7, from 290 mg of 7-[2-(2-propenyloxyimino)-2-(2-tritylaminothiazole-4-yl) acetamide]-3-(3-acetyl-1-imidazoliomethyl)-3-cephem-1-oxido-4-carboxylic acid p-methoxybenzyl ester*iodide (syn-isomer) was obtained 24 mg of 7-[2-(2-aminothiazole-4-yl)-2-(2-propenyloxyimino) acetamide]-3-(3-acetyl-1-imidazoliomethyl)-3-cephem-4-carboxylate (syn-isomer).

NMR δ ppm (DMSO-$d_6$): 1.90(3H,s), 3.5–3.8(2H,m), 4.8(2H,m), 5.1–5.6(2H,m), 5.80(1H,m), 6.69(1H,s), 7.20(2H,s), 9.4(1H,d,J=8.0 Hz).

EXAMPLE 30

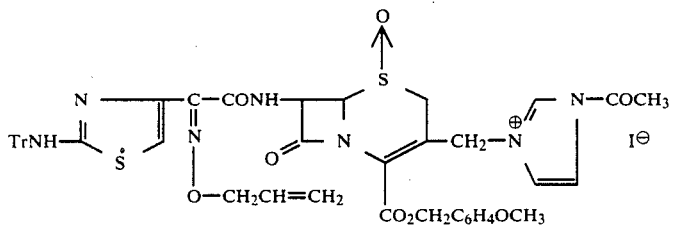

In the same manner as in Example 4, from 0.5 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 50 μl of 1-acetylimidazole was obtained 302 mg of 7-[2-(2-propenyloxyimino)-2-(2-tritylaminothiazole-4-yl) acetamide]-3-(3-acetyl-1-imidazoliomethyl)-3-cephem-1-oxido-4-carboxylic acid p-methoxybenzyl ester*iodide (syn-isomer).

NMR δ ppm (DMSO-$d_6$-TFA-d): 1.90(3H,s), 3.5–3.8(2H,m), 4.8(2H,m), 5.1–5.6(4H,m), 5.80(1H,m), 7.0(1H,s), 7.25(15H,s).

EXAMPLE 31

EXAMPLE 32

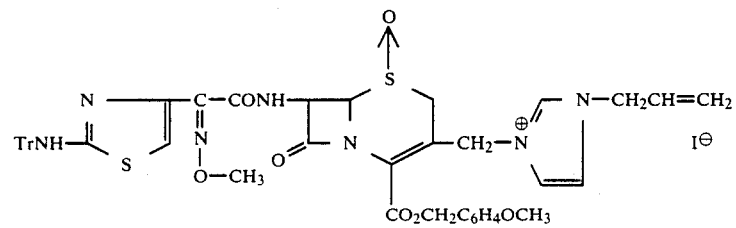

In the same manner as in Example 4, from 0.6 g of 7-[2-methoxyimino-2-(2-tritylaminothiazole-4-yl) acetamide]-3-iodomethyl-3-cephem-1-oxido-4-carboxylic acid p-methoxybenzyl ester (syn-isomer) and 79 mg of 1-(2-propenyl)imidazole was obtained 390 mg of 7-[2-methoxyimino-2-(2-tritylaminothiazole-4-yl) acetamide]-3-[3-(2-propenyl)-1-imidazoliomethyl]-3-cephem-1-oxido-4-carboxylic acid p-methoxybenzyl ester*iodide (syn-isomer).

NMR δ ppm (CDCl$_3$): 3.77(3H,s), 4.0(3H,s), 4.95 (1H,d,J=4 Hz), 5.6–6.5(2H,m), 6.65(1H,s), 6.7–7.5(19H,m), 7.7(1H,s), 9.7(1H,s).

EXAMPLE 33

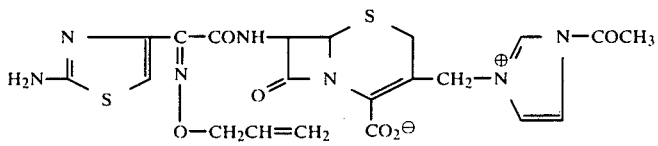

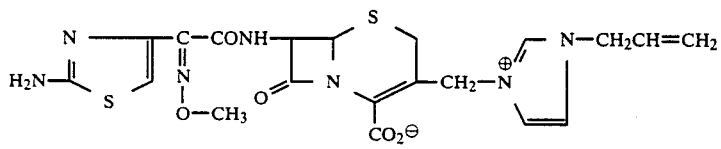

In the same manner as in Examples 5, 6 and 7, from 320 mg of 7-[2-methoxyimino-2-(2-tritylaminothiazole-4-yl) acetamide]-3-[3-(2-propenyl) -1-imidazoliomethyl]-3-cephem-1-oxido-4-carboxylic acid p-methoxybenzyl ester*iodide (syn-isomer) was obtained 26 mg of 7-[2-(2-aminothiazole-4-yl)-2-methoxyiminoacetamide]-3-[3-(2-propenyl)-1-imidazoliomethyl]-3-cephem-4-carboxylate (syn-isomer).

NMR δ (DMSO-d6): 3.80(3H,s), 4.48–6.25(m8H), 6.65(1H,s), 7.1(2H,s), 7.6(1H,s), 7.95(1H,s), 9.25(1H,s), 9.4(1H,d,J=8.0 Hz).

In the same manner as in Examples 5, 6 and 7, from 200 mg of 7-[2-(2-propenyloxyimino)-2-(2-tritylaminothiazole-4-yl) acetamide]-3-(1-imidazoliomethyl)-3-cephem-1-oxido-4-carboxylic acid p-methoxybenzyl ester*iodide (syn-isomer) was obtained 19 mg of 7-[2-(2-aminothiazole-4-yl)-2-(2-propenyloxyimino) acetamide]-3-(1-imidazoliomethyl)-3-cephem-4-carboxylate (syn-isomer).

NMR δ ppm (DMSO-d6): 3.80(3H,s), 4.95(1H,d,J=4.0 Hz), 5.50(1H,m), 6.70(1H,s), 7.5(1H,s), 7.30(1H,s), 7.70(1H,s), 9.4(1H,d,J=6.0 Hz).

EXAMPLE 34

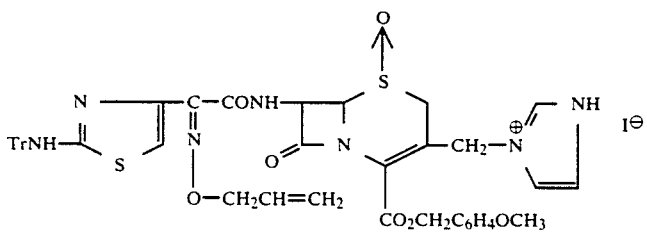

EXAMPLE 36

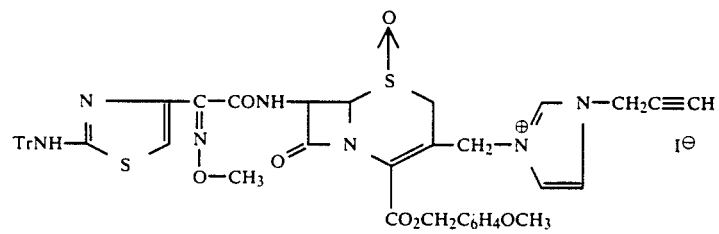

In the same manner as in Example 4, from 1.58 g of 7-[2-(2-propenyloxyimino)-2-(2-tritylaminothiazole-4-yl) acetamide]-3-iodomethyl-3-cephem-1-oxido-4-carboxylic acid p-methoxybenzyl ester (syn-isomer) and 45 μl of imidazole was obtained 250 mg of 7-[2-(2-propenyloxyimino)-2-(2-tritylaminothiazole-4-yl) acetamide]-3-(1-imidazoliomethyl)-3-cephem-1-oxido-4-carboxylic acid p-methoxybenzyl ester*iodide (syn-isomer).

NMR δ ppm (DMSO-d6): 3.80(3H,s), 4.95(1H,d,J=4.0 Hz), 5.50(1H,m), 6.70(1H,s), 6.80–7.75(20H,m), 9.40(1H,d,J=6.0 Hz).

In the same manner as in Example 4, from 0.6 g of 7-[2-methoxyimino-2-(2-tritylaminothiazole-4-yl) acetamide]-3-iodomethyl-3-cephem-1-oxido-4-carboxylic acid p-methoxybenzyl ester (syn-isomer) and 88 mg of 1-propynylimidazole was obtained 330 mg of 7-[2-methoxyimino-2-(2-tritylaminothiazole-4-yl) acetamide]-3-[3-(2-propynyl)-1-imidazoliomethyl]-3-cephem-1-oxido-4-carboxylic acid p-methoxybenzyl ester*iodide (syn-isomer).

NMR δ ppm (CDCl3): 2.75(1H,m), 3.75(3H,s), 4.0(3H,s), 4.75(1H,d,J=3.0 Hz), 4.8–5.5(6H,m), 6.0–6.3(1H,m), 6.70(1H,s), 6.8–7.75(20H,m), 9.8(1H,s).

EXAMPLE 35

EXAMPLE 37

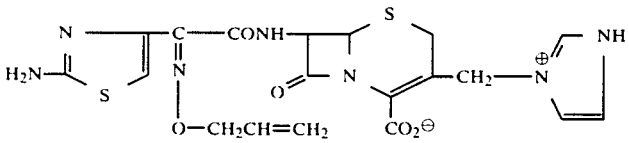

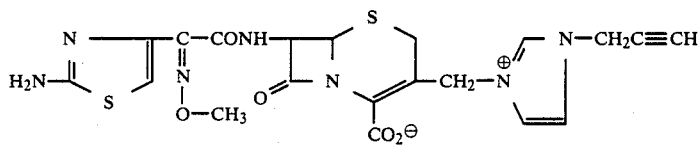

In the same manner as in Examples 5, 6 and 7, from 300 mg of 7-[2-methoxyimino-2-(2-tritylaminothiazole-4-yl) acetamide]-3-[3-(2-propynyl)-1-imidazoliomethyl]-3-cephem-1-oxido-4-carboxylic acid p-methoxybenzyl ester*iodide (syn-isomer) was obtained 52 mg of 7-[2-(2-aminothiazole-4-yl)-2-methoxyiminoacetamide]-3-[3-(2-propynyl)-1-imidazoliomethyl]-3-cephem-4-carboxylate (syn-isomer).

NMR δ ppm (DMSO-$d_6$): 3.80(3H,s), 4.75–5.25(5H,m), 5.5(1H,m), 6.65(1H,s), 7.1(2H,s), 7.65(1H,s), 7.95(1H,s), 9.35(1H,d,J=8.0 Hz), 9.45(1H,s).

In the same manner as in Examples 5, 6 and 7, from 350 mg of 7-[2-methoxyimino-2-(2-tritylaminothiazole-4-yl) acetamide]-3-(3-butyl-1-imidazoliomethyl)-3-cephem-1-oxido-4-carboxylic acid p-methoxybenzyl ester*iodide (syn-isomer) was obtained 60 mg of 7-[2-(2-aminothiazole-4-yl)-2-methoxyiminoacetamide]-3-(3-butyl-1-imidazoliomethyl)-3-cephem-4-carboxylate (syn-isomer).

NMR δ ppm (DMSO-$d_6$): 0.78–1.8(9H,m), 3.75(3H,s), 4.95(1H,d,J=4.0 Hz), 5.50(1H,m), 6.70(1H,s), 7.10(2H,s), 7.70(1H,s), 8.0(1H,s), 9.25(1H,s), 9.4(1H,d,J=8.0 Hz).

EXAMPLE 38

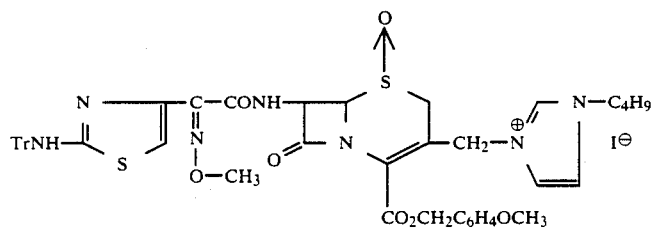

In the same manner as in Example 4, from 0.54 g of 7-[2-methoxyimino-2-(2-tritylaminothiazole-4-yl)acetamide]-3-iodomethyl-3-cephem-1-oxido-4-carboxylic acid p-methoxybenzyl ester (syn-isomer) and 80 mg of 1-butylimidazole was obtained 365 mg of 7-[2-methoxyimino-2-(2-tritylaminothiazole-4-yl) acetamide]-3-(3-butyl-1-imidazoliomethyl)-3-cephem-1-oxido-4-carboxylic acid p-methoxybenzyl ester*iodide (syn-isomer).

NMR δ ppm (DMSO-$d_6$): 3.8(3H,s), 4.0(3H,s), 6.2(1H,m), 6.7(1H,s), 6.8–7.5(19H,m), 7.75(1H,s), 9.7(1H,s).

EXAMPLE 39

EXAMPLE 40

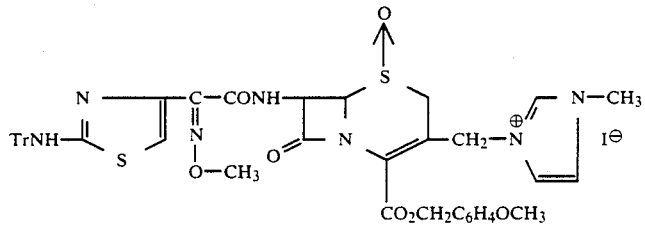

In the same manner as in Example 4, from 1.37 g of 7-[2-methoxyimino-2-(2-tritylaminothiazole-4-yl)acetamide]-3-iodomethyl-3-cephem-1-oxido-4-carboxylic acid p-methoxybenzyl ester (syn-isomer) and 120 μl of 1-methylimidazole was obtained 650 mg of 7-[2-methoxyimino-2-(2-tritylaminothiazole-4-yl)-acetamide]-3-(3-methyl-1-imidazoliomethyl)-3-cephem-1-oxido-4-carboxylic acid p-methoxybenzyl ester*iodide (syn-isomer).

NMR δ ppm (DMSO-$d_6$): 3.74(3H,s), 3.80(3H,s), 3.82(3H,s), 4.95(1H,d,J=4.0 Hz), 5.75(1H,m), 6.75(1H,s).

EXAMPLE 41

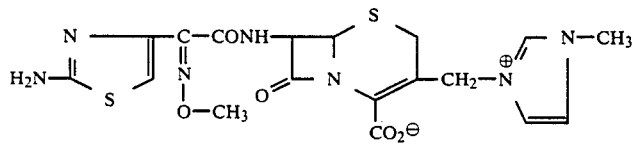

In the same manner as in Examples 5, 6 and 7, from 600 mg of 7-[2-methoxyimino-2-(2-tritylaminothiazole-4-yl) acetamide]-3-(3-methyl-1-imidazoliomethyl)-3-cephem-1-oxido-4-carboxylic acid p-methoxybenzyl ester*iodide (syn-isomer) was obtained 42 mg of 7-[2-(2-aminothiazole-4-yl)-2-methoxyiminoacetamide]-3-(3-methyl-1-imidazoliomethyl)-3-cephem-4carboxylate.

NMR δ ppm (DMSO-d$_6$): 3.8(3H,s), 5.0(1H,d,J=4.0 Hz), 5.6(1H,m), 6.7(1H,s), 7.2(2H,s), 7.7(s,1H), 7.9(1H,s), 9.2(1H,s), 9.4(1H,d,J=8.0 Hz).

EXAMPLE 42

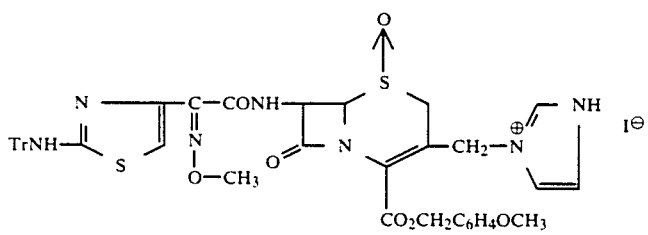

In the same manner as in Example 4, from 0.5 g of 7-[2-methoxyimino-2-(2-tritylaminothiazole-4-yl) acetamide]-3-iodomethyl-3-cephem-4-carboxylic acid p-methoxybenzyl ester (syn-isomer) and 45 μl of imidazole was obtained 331 mg of 7-[2-methoxyimino-2-(2-tritylaminothiazole-4-yl) acetamide]-3-(1-imidazoliomethyl)-3-cephem-1-oxido-4-carboxylic acid p-methoxybenzyl ester*iodide (syn-isomer).

NMR δ ppm (DMSO-d$_6$): 3.80(3H,s), 4.95(1H,d,J=4.0 Hz), 5.50(1H,m), 6.70(1H,s), 7.25(15H,s), 7.30(1H,s), 7.70(1H,s), 9.4(1H,d,J=6.0 Hz).

EXAMPLE 43

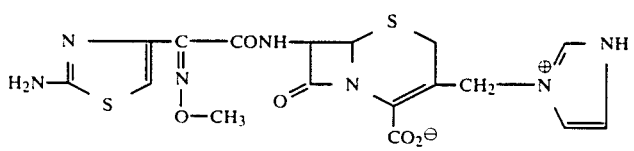

In the same manner as in Examples 5, 6 and 7, from 320 mg of 7-[2-methoxyimino-2-(2-tritylaminothiazole-4-yl) acetamide]-3-(1-imidazoliomethyl)-3-cephem-1-oxido-4-carboxylic acid p-methoxybenzyl ester*iodide (syn-isomer) was obtained 38 mg of 7-[2-(2amino-thiazole-4-yl)-2-methoxyiminoacetamide]-3-(1-imidazoliomethyl)-3-cephem-4-carboxylate (syn-isomer).

NMR δ ppm (DMSO-d$_6$): 3.80(3H,s), 4.95(1H,d,J=4.0 Hz), 5.50(1H,m), 6.70(1H,s), 6.80(2H,s), 7.15(1H,s), 7.30(1H,s), 7.70(1H,s), 9.4(1H,d,J=6.0 Hz).

EXAMPLE 44

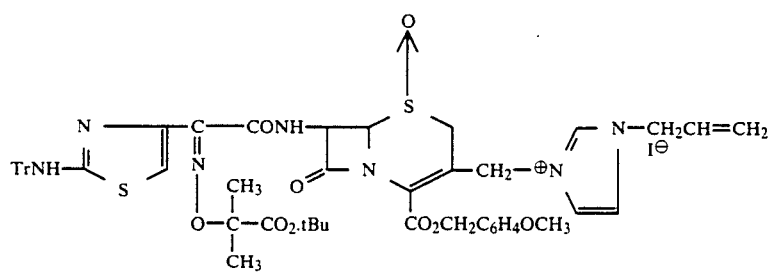

Into a mixture of THF (5 ml) and chloroform (2.5 ml) was dissolved 0.6 g of 7-[2-(2-tert-butoxycarbonyl)-prop-2-oxyimino-2-(2-tritylaminothiazole-4-yl)acetamide]-3-iodomethyl-3-cephem-1-oxido-4-carboxylic acid p-methoxybenzyl ester (syn-isomer). To the solution which was cooled to 0° C. was added 70 mg of 1-(2-propenyl)imidazole. After the addition, the mixture was heated to room temperature and was further stirred for 3 hours. A solvent was removed at a reduced pressure. The residue was made into a powder with use of 50 ml of diethyl ether and eluted by a silicagel column (chloroform/methanol=8/1, volume ratio) to obtain 412.2 mg of 7-[2-(2-tert-butoxycarbonyl)prop-2-oxyimino-2-(2-tritylaminothiazole-4-yl)acetamide]-3-[3-(2-propenyl)-1-imidazoliomethyl]-3-cephem-1-oxido-4-carboxylic acid p-methoxybenzyl ester.iodide (syn-isomer).

NMR δ ppm (DMSO-d$_6$): 1.36(15H,s), 3.75(2H,m), 3.79(3H,s), 4.83(2H,m), 5.00(1H,m), 5.07–5.53(6H,m), 5.75–5.95(2H,m), 6.73(1H,s), 7.18(4H,m), 7.23(15H,s), 7.70(2H,m), 8.75(1H,s), 9.23(1H,m), 9.42(1H,s).

EXAMPLE 45

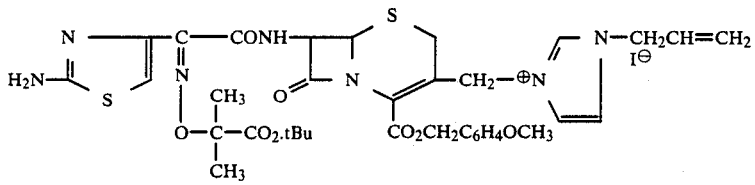

In the same manner as in Examples 5 and 6, from 400 mg of 7-[2-(2-tert-butoxycarbonyl)prop-2-oxyimino-2-(2-tritylaminothiazole-4-yl)acetamide]-3-[3-(2-propenyl)-1-imidazoliomethyl]-3-cephem-1-oxido-4-carboxylic acid p-methoxybenzyl ester.iodide (syn-isomer) was obtained 230 mg of 7-[2-(2-aminothiazole-4-yl)-2-(2-tert-butoxycarbonyl)prop-2-oxyiminoacetamide]-3-[3-(2-propenyl)-1-imidazoliomethyl]-3-cephem-4-carboxylic acid p-methoxybenzyl ester.iodide (syn-isomer).

NMR δ ppm (DMSO-d$_6$): 1.37(9H,s), 1.49(3H,s), 1.52(3H,s), 3.50(2H,s), 3.76(3H,s), 4.82(2H,s), 4.90–5.52(7H,m), 5.72–6.31(2H,m), 6.69(1H,s), 7.13(4H,m), 7.22(2H,s), 7.66(2H,m), 9.21(1H,s), 9.30(1H,m).

EXAMPLE 46

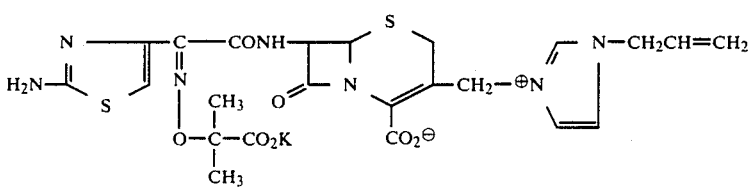

Into a mixture of methylene chloride (3 ml) and anisole (2.2 ml) was dissolved 220 mg of 7-[2-(2-aminothiazole-4-yl)-2-(2-tert-butoxycarbonyl)prop-2-oxyiminoacetamide]-3-[3-(2-propenyl)-1-imidazoliomethyl]-3-cephem-4-carboxylic acid p-methoxybenzyl ester.iodide (syn-isomer). To the solution which was cooled to 0° C. was added 3.1 ml of trifluoroacetic acid. The mixture was stirred at 0° C. for 2 hours and then at 10° C. for 4 hours. A solvent was removed at a reduced pressure. The residue was made into a powder with use of 50 ml of diethyl ether, collected by filtration, neutralized with an aqueous solution of potassium hydrogen carbonate and freeze-dried, giving yellow powder. The powder was eluted by use of Sephadex LH-20 (methanol) to obtain 53.2 mg of white powder of 7-{2-(2-aminothiazole-4-yl)-2-[potassium(2,2-dimethylacetate)oxyimino]acetamide}-3-[3-(2-propenyl)-1-imidazoliomethyl]-3-cephem-4-carboxylate (syn-isomer).

NMR δ ppm (DMSO-d$_6$): 1.38(3H,s), 1.43(3H,s), 3.50(2H,s), 4.83(2H,m), 4.91–5.60(5H,m), 5.75–6.37(2H,m), 6.68(1H,s), 7.07(2H,s), 7.58(1H,s), 7.48(1H,s), 9.46(1H,s), 12.13(1H,m).

EXAMPLE 47

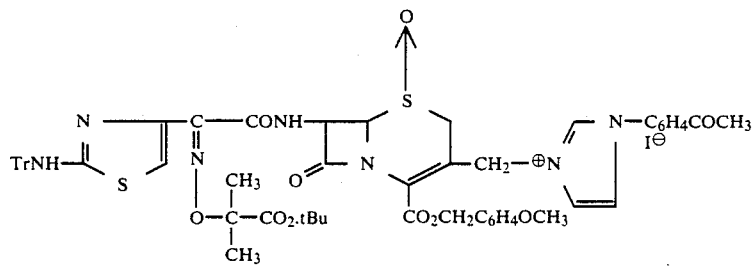

In the same manner as in Example 44, from 0.5 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 100 μl of 4-imidazole acetophenone was obtained 340 mg of 7-[2-(2-tert-butoxycarbonyl)prop-2-oxyimino-2-(2-tritylaminothiazole-4-yl)acetamide]-3-(3-acetophenyl-1-imidazoliomethyl)-3-cephem-1-oxido-4-carboxylic acid p-methoxybenzyl ester.iodide (syn-isomer).

NMR δ ppm (DMSO-d$_6$): 1.36(15H,s), 3.75(2H,m), 3.60(3H,s), 4.83(2H,m), 6.73(1H,s), 7.18(4H,m), 7.25(15H,s), 9.42(1H,d,J=8.0Hz).

EXAMPLE 48

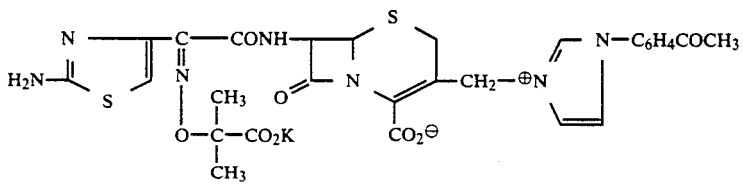

In the same manner as in Examples 45 and 46, from 330 mg of 7-[2-(2-tert-butoxycarbonyl)prop-2-oxyimino-2-(2-tritylaminothiazole-4-yl)acetamide]-3-(3-acetophenyl-1-imidazoliomethyl)-3-cephem-1-oxido-4-carboxylic acid p-methoxybenzyl ester.iodide (syn-isomer) was obtained 53 mg of 7-{2-(2-aminothiazole-4-yl)-2-[potassium(2,2-dimethylacetate)oxyimino]acetamide}-3-(3-acetophenyl-1-imidazoliomethyl)-3-cephem-4-carboxylate (syn-isomer).

NMR δ ppm (DMSO-$d_6$): 3.60(3H,s), 4.83(2H,m), 6.69(1H,s), 7.13(2H,s), 7.66(2H,m), 9.30(1H,d,J=8.0Hz).

EXAMPLE 49

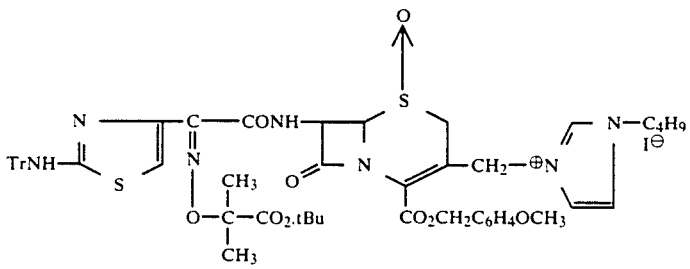

In the same manner as in Example 44, from 0.6 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 80 mg of 1-butylimidazole was obtained 410 mg of 7-[2-(2-tert-butoxycarbonyl)prop-2-oxyimino-2-(2-tritylaminothiazole-4-yl)acetamide]-3-(3-butyl-1-imidazoliomethyl)-3-cephem-1-oxido-4-carboxylic acid p-methoxybenzyl ester.iodide (syn-isomer).

NMR δ ppm (CDCl$_3$): 0.97(3H,m), 1.40(9H,s), 1.53(6H,s), 1.6–2.11(4H,m), 3.68(3H,s), 4.00(2H,s), 4.13(2H,m), 4.97(1H,d), 5.21(2H,s), 5.48(2H,m), 6.22(1H,m), 6.52(1H,s), 7.13(4H,m), 7.25(15H,s), 7.26(1H,s), 9.72(1H,s).

EXAMPLE 50

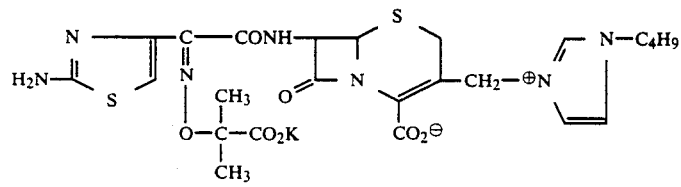

In the same manner as in Examples 45 and 46, from 385 mg of 7-[2-(2-tert-butoxycarbonyl)prop-2-oxyimino-2-(2-tritylaminothiazole-4-yl)acetamide]-3-(3-butyl-1-imidazoliomethyl)-3-cephem-1-oxido-4-carboxylic acid p-methoxybenzyl ester.iodide (syn-isomer) was obtained 51 mg of 7-{2-(2-aminothiazole-4-yl)-2-[potassium(2,2-dimethylacetate)oxyimino]acetamide}-3-(3-butyl-1-imidazoliomethyl)-3-cephem-4-carboxylate (syn-isomer).

NMR δ ppm (DMSO-$d_6$): 0.85(3H,m), 1.36(3H,s), 1.40(3H,s), 3.46(2H,s), 4.12(2H,m), 5.67(1H,m), 6.64(1H,s), 7.10(2H,s), 7.64(1H,s), 7.9(1H,s), 9.46(1H,s), 11.95(1H,m).

EXAMPLE 51

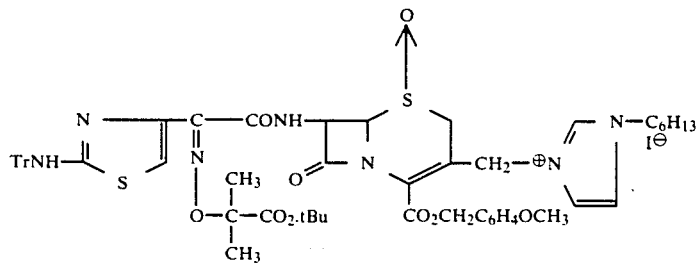

In the same manner as in Example 44, from 0.6 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 80 mg of 1-n-hexylimidazole was obtained 360 mg of 7-[2-(2-tert-butoxycarbonyl)prop-2-oxyimino-2-(2-tritylaminothiazole-4-yl)acetamide]-3-(3-n-hexyl-1-imidazoliomethyl)-3-cephem-1-oxido-4-carboxylic acid p-methoxybenzyl ester.iodide (syn-isomer).

NMR δ ppm (CDCl₃): 0.88(3H,m), 1.05–2.15(8H,m), 1.39(9H,s), 2.04(6H,s), 3.76(3H,s), 5.02(1H,m), 5.43(2H,m), 6.14(1H,m), 6.48(1H,s), 7.02(4H,m), 7.24(15H,s), 7.73(1H,s), 9.64(1H,s).

EXAMPLE 52

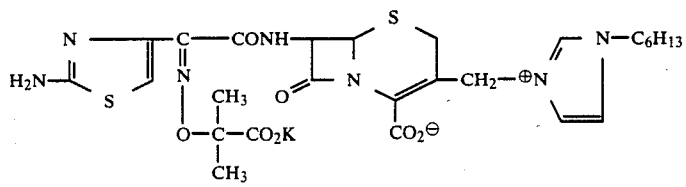

In the same manner as in Examples 45 and 46, from 345 mg of 7-[2-(2-tert-butoxycarbonyl)prop-2-oxyimino-2-(2-tritylaminothiazole-4-yl)acetamide]-3-(3-n-hexyl-1-imidazoliomethyl)-3-cephem-1-oxido-4-carboxylic acid p-methoxybenzyl ester.iodide (syn-isomer) was obtained 23 mg of 7-{2-(2-aminothiazole-4-yl)-2-[potassium(2,2-dimethylacetate)oxyimino]acetamide}-3-(3-n-hexyl-1-imidazoliomethyl)-3-cephem-4-carboxylate (syn-isomer).

NMR δ ppm (DMSO-d₆): 0.82(3H,t,J=6.5Hz), 4.08(2H,t,J=6.5Hz), 0.98–2.05(4H,m), 4.93(1H,d,J=5.0Hz), 1.34(3H,s), 5.63(1H,d,d,J=5.0Hz,J=8.0Hz), 1.38(3H,s), 6.64(1H,s), 3.43(2H,s), 7.07(2H,s), 7.62(1H,s), 7.92(1H,s), 9.39(1H,s), 11.75(1H,d,J=8.0Hz).

EXAMPLE 53 cephem-1-oxido-4-carboxylic acid p-methoxybenzyl ester (syn-isomer) and 127 mg of 1-n-dodecanylimidazole was obtained 296 mg of 7-[2-(2-tert-butoxycarbonyl)prop-2-oxyimino-2-(2-tritylaminothiazole-4-yl)acetamide]-3-(3-n-dodecanyl-1-imidazoliomethyl)-3-cephem-1-oxido-4-carboxylic acid p-methoxybenzyl ester.iodide (syn-isomer).

NMR δ ppm (DMSO-d₆): 0.84(3H,m), 0.9–2.3(20H,m), 1.33(9H,s), 1.40(6H,s), 3.60(2H,m), 3.74(3H,s), 4.96(1H,m), 5.22(2H,s), 5.84(1H,m), 6.73(1H,s), 7.25(15H,s), 7.75(1H,s), 8.07(1H,m), 9.01(1H,s).

EXAMPLE 54

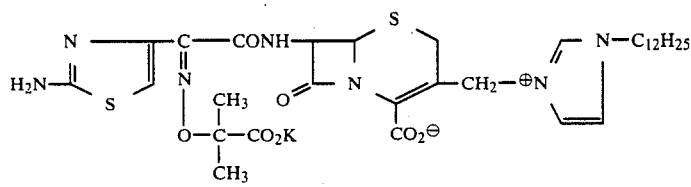

In the same manner as in Examples 45 and 46, from 290 mg of 7-[2-(2-tert-butoxycarbonyl)prop-2-oxyimino-2-(2-tritylaminothiazole-4-yl)acetamide]-3-(3-n-dodecanyl-1-imidazoliomethyl)-3-cephem-1-oxido-4-carboxylic acid p-methoxybenzyl ester.iodide (syn-isomer) was obtained 31.5 mg of 7-{2-(2-aminothiazole-4-yl)-2-[potassium(2,2-dimethylacetate)oxyimino]acetamide}-3-(3-n-dodecanyl-1-imidazoliomethyl)-3-cephem-4-carboxylate (syn-isomer).

NMR δ ppm (DMSO-d₆): 0.84(3H,m), 0.96–2.05(20H,m), 1.35(3H,s), 1.40(3H,s), 3.50(2H,s), 3.68(2H,m), 4.93(1H,m), 4.98(2H,m), 5.64(1H,m), 6.65(1H,s), 7.08(2H,s), 7.64(1H,s), 7.95(1H,s), 9.35(1H,s), 11.50(1H,m).

EXAMPLE 55

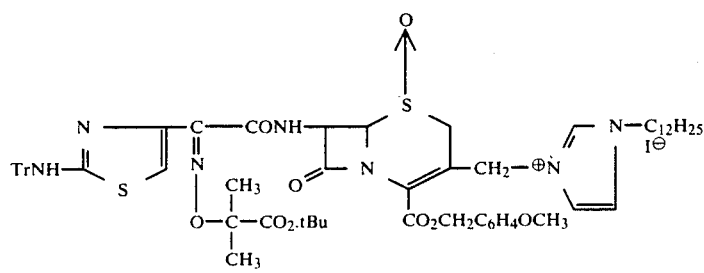

In the same manner as in Example 44, from 0.5 g of 7-[2-(2-tert-butoxycarbonyl)prop-2-oxyimino-2-(2-tritylaminothiazole-4-yl)acetamide]-3-iodomethyl-3-

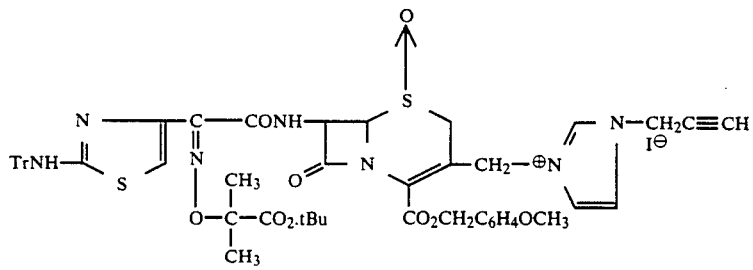

In the same manner as in Example 44, from 0.5 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 57 mg of 1-(2-propynyl-)imidazole was obtained 294 mg of 7-[2-(2-tert-butoxycarbonyl)prop-2-oxyimino-2-(2-tritylaminothiazole-4-yl)acetamide]-3-[3-(2-propynyl)-1-imidazoliomethyl]-3-cephem-1-oxido-4-carboxylic acid p-methoxybenzyl ester.iodide (syn-isomer).

NMR δ ppm (CDCl$_3$): 1.41(9H,s), 1.57(6H,s), 3.80(3H,s), 5.24(2H,s), 6.40(1H,m), 6.57(1H,s), 7.06(4H,m), 7.28(15H,s).

EXAMPLE 56

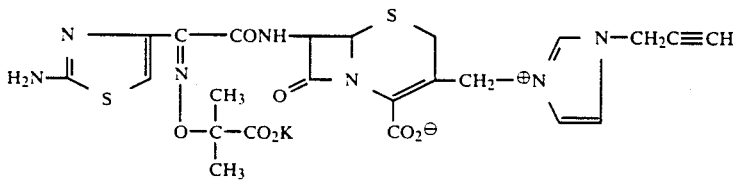

In the same manner as in Examples 45 and 46, from 290 mg of 7-[2-(2-tert-butoxycarbonyl)prop-2-oxyimino-2-(2-tritylaminothiazole-4-yl)acetamide]-3-[3-(2-propynyl)-1-imidazoliomethyl]-3-cephem-1-oxido-4-carboxylic acid p-methoxybenzyl ester.iodide (syn-isomer) was obtained 34.2 mg of 7-{2-(2-aminothiazole-4-yl)-2-[potassium(2,2-dimethylacetate)ox-yimino]acetamide}-3-[3-(2-propynyl)-1-imidazoliomethyl]-3-cephem-4-carboxylate (syn-isomer).

NMR δ ppm (DMSO-d$_6$): 1.40(3H,s), 1.45(3H,s), 3.62(2H,s), 3.72(1H,m), 4.50–5.45(5H,m), 5.32(1H,m), 6.74(1H,s), 7.15(2H,s), 7.64(1H,s), 7.96(1H,s), 9.15(1H,s), 11.88(1H,m).

EXAMPLE 57

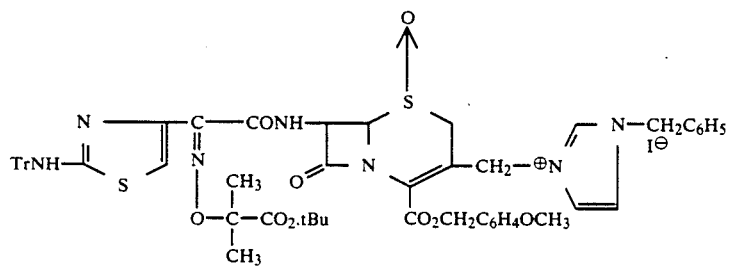

In the same manner as in Example 44, from 0.6 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 101 mg of 1-benzylimidazole was obtained 409 mg of 7-[2-(2-tert-butoxycarbonyl)prop-2-oxyimino-2-(2-tritylaminothiazole-4-yl)acetamide]-3-(3-benzyl-1-imidazoliomethyl)-3-cephem-1-oxido-4-carboxylic acid p-methoxybenzyl ester.iodide (syn-isomer).

NMR δ ppm (DMSO-d$_6$): 1.36(15H,s), 3.65(2H,m), 3.73(3H,s), 4.85–5.32(5H,m), 5.42(2H,s), 5.72(1H,m), 6.63(1H,s), 7.13(4H,m), 7.28(15H,s), 7.42(5H,s), 7.71(2H,m), 8.76(1H,s), 9.23(1H,m), 9.32(1H,s).

EXAMPLE 58

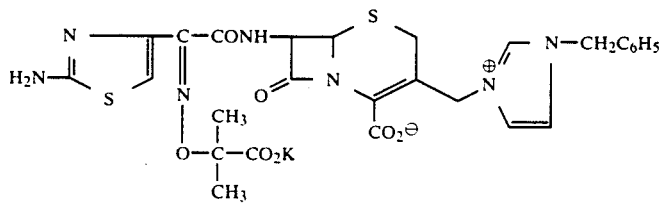

In the same manner as in Examples 45 and 46, from 480 mg of 7-[2-(2-tert-butoxycarbonyl)prop-2-oxyimino-2-(2-tritylaminothiazole-4-yl)acetamide]-3-(3- benzyl-1-imidazoliomethyl)-3-cephem-1-oxido-4-carboxylic acid p-methoxybenzyl ester.iodide (syn-isomer) was obtained 38.9 mg of 7-{2-(2-aminothiazole-4-yl)-2-[potassium(2,2-dimethylacetate)oxyimino]acetamide}-3-(3-benzyl-1-imidazoliomethyl)-3-cephem-4-carboxylate (syn-isomer).

NMR δ ppm (DMSO-d$_6$): 1.34(9H,s), 1.43(6H,s), 3.50(2H,s), 5.45(2H,s), 5.68(1H,m), 6.72(1H,s), 7.12(2H,s), 7.42(5H,s), 7.64(1H,s), 8.03(1H,s), 9.65(1H,s), 12.01(1H,m).

EXAMPLE 59 oxyimino-2-(2-tritylaminothiazole-4-yl)acetamide]-3-(3-methyl-1-imidazoliomethyl)-3-cephem-1-oxido-4-carboxylic acid p-methoxybenzyl ester.iodide (syn-isomer) was obtained 50.9 mg of 7-{2-(2-aminothiazole-4-yl)-2-[potassium(2,2-dimethylacetate)oxyimino]acetamide}-3-(3methyl-1-imidazoliomethyl)-3-cephem-4-carboxylate (syn-isomer).

NMR δ ppm (DMSO-d$_6$): 1.39(3H,s), 1.45(3H,s), 3.48(2H,s), 4.84(3H,s), 4.97(1H,m), 4.99(2H,m), 5.73(1H,m), 6.71(1H,s), 7.12(2H,s), 7.57(1H,s), 7.95(1H,s), 9.48(1H,s), 12.06(1H,m).

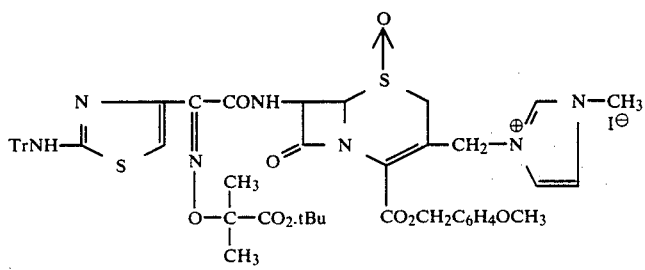

In the same manner as in Example 44, from 0.6 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 50 μl of 1-methylimidazole was obtained 339 mg of 7-[2-(2-tert-butoxycarbonyl)prop-2-oxyimino-2-(2-tritylaminothiazole-4-yl)acetamide]-3-(3-methyl-1-imidazoliomethyl)-3-cephem-1-oxido-4-carboxylic acid p-methoxybenzyl ester.iodide (syn-isomer).

NMR δ ppm (DMSO-d$_6$): 1.36(15H,s), 3.70(2H,m), 3.75(3H,s), 3.83(3H,s), 4.80–5.46(5H,m), 5.68(1H,m), 6.67(1H,s), 7.22(15H,s), 8.26(1H,s), 9.08(1H,s), 9.23(1H,m).

EXAMPLE 60

EXAMPLE 61

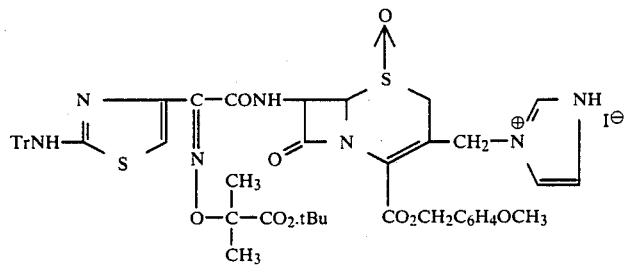

In the same manner as in Example 44, from 0.5 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 50 μl of imidazole was obtained 280 mg of 7-[2-(2-tert-butoxycarbonyl)prop-2-oxyimino-2-(2-tritylaminothiazole-4-yl)acetamide]-3-(1-imidazoliomethyl)-3-cephem-1-oxido-4-carboxylic acid p-methoxybenzyl ester.iodide (syn-isomer).

NMR δ ppm (DMSO-d$_6$): 1.34(9H,s), 1.42(6H,s), 3.53(2H,m), 3.75(3H,s), 5.26(2H,s), 5.86(1H,m), 6.75(1H,s), 7.09(1H,s), 7.26(15H,s), 7.42(1H,s), 7.60(1H,s), 8.02(1H,m), 8.63(1H,s).

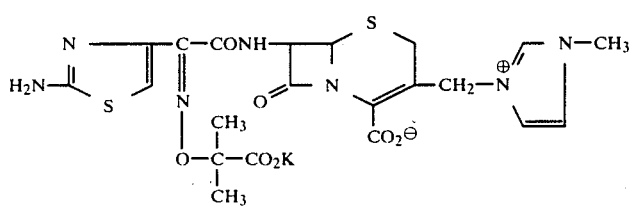

In the same manner as in Examples 45 and 46, from 320 mg of 7-[2-(2-tert-butoxycarbonyl)prop-2-

EXAMPLE 62

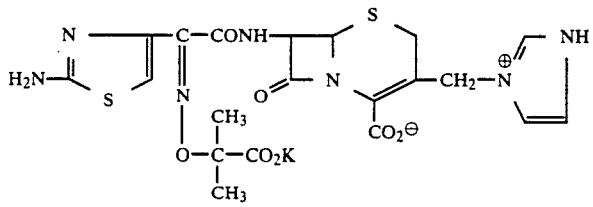

In the same manner as in Examples 45 and 46, from 270 mg of 7-[2-(2-tert-butoxycarbonyl)prop-2-oxyimino-2-(2-tritylaminothiazole-4-yl)acetamide]-3-(1-imidazoliomethyl)-3-cephem-1-oxido-4-carboxylic acid p-methoxybenzyl ester.iodide (syn-isomer) was obtained 30 mg of 7-{2-(2-aminothiazole-4-yl)-2-[potassium(2,2-dimethylacetate)oxyimino]acetamide}-3-(1-imidazoliomethyl)-3-cephem-4carboxylate (syn-isomer).

NMR δ ppm (DMSO-$d_6$): 1.36(3H,s), 1.41(3H,s), 3.46(2H,s), 4.91(1H,m), 5.50(1H,m), 6.67(1H,s), 7.05(2H,s), 7.20(1H,s), 7.61(1H,s), 12.00(1H,m).

EXAMPLE 63

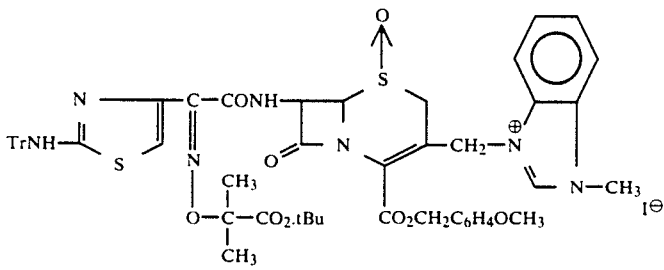

In the same manner as in Example 44, from 0.5 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 71.3 mg of 1-methylbenzimidazole was obtained 294 mg of 7-[2-(2-tert-butoxycarbonyl)prop-2-oxyimino-2-(2-tritylaminothiazole-4-yl)acetamide]-3-(benz-3-N-methyl-1-imidazoliomethyl)-3-cephem-1-oxido-4-carboxylic acid p-methoxybenzyl ester.iodide (syn-isomer).

NMR δ ppm (DMSO-$d_6$): 1.32(9H,s), 1.37(6H,s), 3.60(2H,m), 3.69(3H,s), 3.80(3H,m), 4.10(3H,s), 5.22(2H,s), 5.45(2H,s), 5.86(1H,m), 6.70(1H,s), 7.09(14H,m), 7.19(15H,s), 8.60(1H,s).

EXAMPLE 64

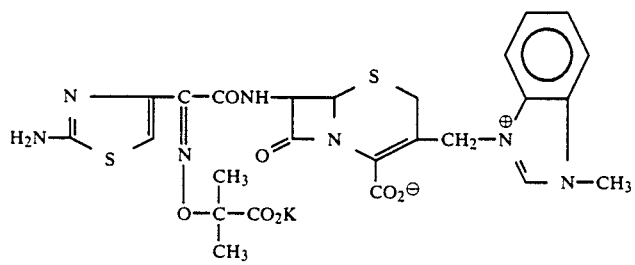

In the same manner as in Examples 45 and 46, from 280 mg of 7-[2-(2-tert-butoxycarbonyl)prop-2-oxyimino-2-(2-tritylaminothiazole-4-yl)acetamide]-3-(benz-3-N-methyl-1-imidazoliomethyl)-3-cephem-1-oxido-4-carboxylic acid p-methoxybenzyl ester.iodide (syn-isomer) was obtained 12 mg of 7-{2-(2-aminothiazole-4-yl)-2-[potassium(2,2-dimethylacetate)oxyimino]acetamide}-3-(benz-3-N-methyl-1-imidazoliomethyl)-3-cephem-4-carboxylate (syn-isomer).

NMR δ ppm (DMSO-$d_6$): 1.41(3H,s), 1.45(3H,s), 3.80(3H,m), 4.89(1H,m), 5.17(2H,m), 5.52(1H,m), 6.72(1H,s), 6.73–7.42(2H,m), 7.12(2H,s), 8.32(1H,s), 12.06(1H,m).

EXAMPLE 65

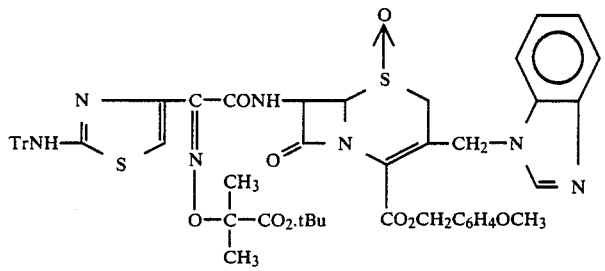

In the same manner as in Example 44, from 0.5 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 67 mg of benzimidazole was obtained 354 mg of 7-[2-(2-tert-butoxycarbonyl)prop-2-oxyimino-2-(2-tritylaminothiazole-4-yl)acetamide]-3-(benz-1-imidazoliomethyl)-3-cephem-1-oxido-4-carboxylic acid p-methoxybenzyl ester.iodide (syn-isomer).

NMR δ ppm (DMSO-$d_6$): 1.32(9H,s), 1.37(6H,s), 3.60(2H,m), 3.69(3H,s), 4.96(1H,m), 5.22(2H,s), 5.45(2H,s), 5.86(1H,m), 6.70(1H,s), 7.09(4H,m), 7.19(15H,s), 8.60(1H,s).

EXAMPLE 66

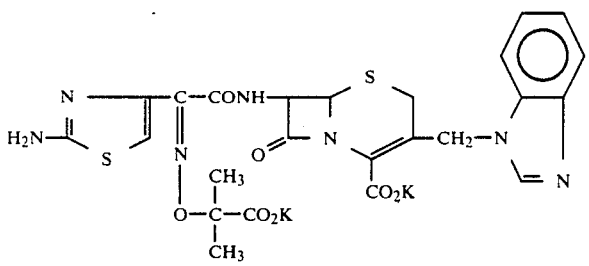

In the same manner as in Examples 45 and 46, from 345 mg of 7-[2-(2-tert-butoxycarbonyl)prop-2-oxyimino-2-(2-tritylaminothiazole-4-yl)acetamide]-3-(benz-1-imidazoliomethyl)-3-cephem-1-oxido-4-carboxylic acid p-methoxybenzyl ester.iodide (syn-isomer) was obtained 21.2 mg of potassium 7-{2-(2-aminothiazole-4-yl)-2-[potassium(2,2-dimethylacetate)oxyimino]acetamide}-3-(benz-1-imidazoliomethyl)-3-cephem-4-carboxylate (syn-isomer).

NMR δ ppm (DMSO-$d_6$): 1.41(3H,s), 1.45(3H,s), 3.47(2H,s), 4.89(1H,m), 5.17(2H,m), 5.52(1H,m), 6.72(1H,s), 6.73–7.42(2H,m), 7.12(2H,s), 8.32(1H,s), 12.06(1H,m).

EXAMPLE 67

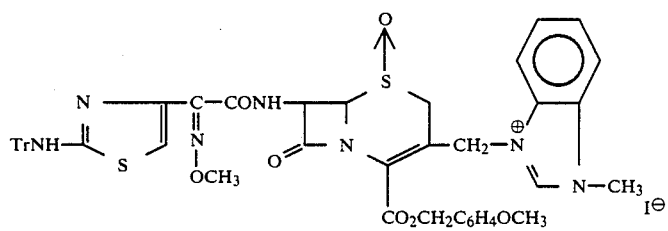

In the same manner as in Example 4, from 0.5 g of 7-[2-methoxyimino-2-(2-tritylaminothiazole-4-yl)acetamide]-3-iodomethyl-3-cephem-1-oxido-4-carboxylic acid p-methoxybenzyl ester (syn-isomer) and 70 mg of 1-methylimidazole was obtained 285 mg of 7-[2-methoxyimino-2-(2-tritylaminothiazole-4-yl)acetamide]-3-(benz-3-N-methyl-1-imidazoliomethyl)-3-cephem-1-oxido-4-carboxylic acid p-methoxybenzyl ester.iodide (syn-isomer).

NMR δ ppm (DMSO-$d_6$): 3.80(3H,m), 4.10(3H,s), 4.90(1H,m), 5.2–5.6(6H,m), 6.60(1H,s), 7.0–7.3(15H,s), 9.2(1H,d,J=8.0Hz).

EXAMPLE 68

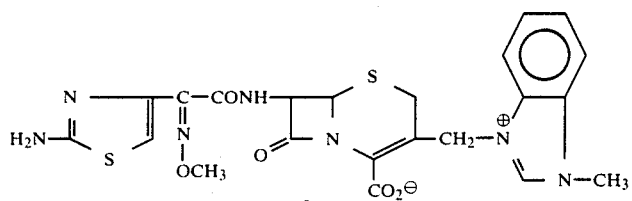

In the same manner as in Examples 5, 6 and 7 from 279 mg of 7-[2-methoxyimino-2-(2-tritylaminothiazole-4-yl)acetamide]-3-(benz-3-N-methyl-1-imidazoliome- thyl)-3-cephem-1-4-carboxylic acid p-methoxybenzyl ester.iodide (syn-isomer) was obtained 20.5 mg of 7-[2-(2-aminothiazole-4-yl)-2-methoxyiminoacetamide]-3-(benz-3-N-methyl-1-imidazoliomethyl)-3-cephem-4-carboxylate (syn-isomer).

NMR δ ppm (DMSO-d$_6$): 3.80(3H,m), 4.10(3H,s), 4.90(1H,m), 5.2–5.6(3H,m), 6.60(1H,s), 7.0(2H,s), 7.6(2H,m), 7.8(1H,m), 9.2(1H,d,J=8.0Hz).

EXAMPLE 69

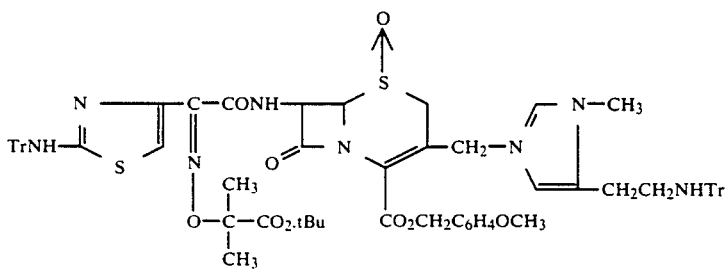

In the same manner as in Example 44, from 0.6 g of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 234 mg of 1-methyl-5-(2-tritylamino)ethylimidazole was obtained 432 mg of 7-[2--(2-tert-butoxycarbonyl)prop-2-oximino-2-(2-tritylaminothiazole-4-yl)acetamide]-3-[3-methyl-4-(2-tritylamino)ethyl-1-imidazoliomethyl]-3-cephem-1-oxido-4-carboxylic acid p-methoxybenzyl ester.iodide (syn-isomer).

NMR δ ppm (CDCl$_3$): 1.42(9H,s), 1.55(6H,s), 2.30-2.92(4H,m), 3.70(3H,s), 3.80(3H,s), 4.02(2H,s), 4.98(1H,m), 5.21(2H,s), 5.29(2H,m), 6.22(H,m), 6.57(1H,s), 7.12(4H,m), 7.21-7.43(30H,s), 7.02-7.64(4H,m), 9.17(1H,s).

EXAMPLE 70

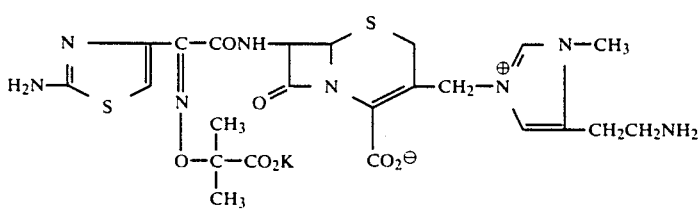

In the same manner as in Examples 43 and 44, from 400 mg of 7-[2-(2-tert-butoxycarbonyl)prop-2-oxyimino-2-(2-tritylaminothiazole-4-yl)acetamide]-3-[3-methyl-4-(2-tritylamino)ethyl-1-imidazoliomethyl]-3-cephem-1-oxido-4-carboxylic acid p-methoxybenzyl ester.iodide (syn-isomer) was obtained 59.4 mg of 7-{2-(2-aminothiazole-4-yl)-2-[potassium(2,2-dimethylacetate)oxyimino]acetamide}-3-[3-methyl-4-(2-amino)ethyl-1-imidazoliomethyl]-3-cephem-4-carboxylate (syn-isomer).

NMR δ ppm (DMSO-d$_6$-TFA-d); 1.56(6H,s), 2.53-3.31(4H,m), 3.52(2H,s), 3.82(3H,s), 4.98(1H,m), 5.17(2H,m), 5.91(1H,m), 6.81(1H,s), 7.02(2H,s), 7.51(2H,s), 8.10(1H,s), 9.17(1H,s), 11.85(1H,s).

EXAMPLE 71

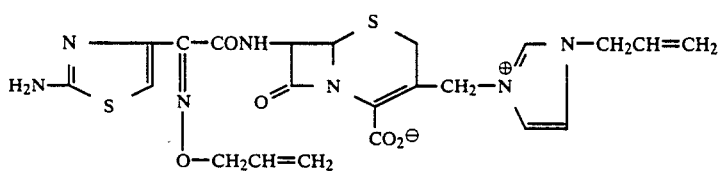

In 20 ml of dry ethyl acetate was suspended 0.56 g of 7-amino-3-[3-(2-propenyl)-1-imidazoliomethyl]-3-cephem-4-carboxylic acid which was obtained from 7-phenylacetamide-3-[3-(2-propenyl)-1-imidazoliomethyl]-3-cephem-4-carboxylic acid p-methoxybenzyl ester (syn-isomer) by a conventional iminoether method. To the suspension was added 4.8 g of bis(trimethylsilyl)acetamide and the mixture was stirred at room temperature (A-solution). Phosphorus oxychloride (0.6 g) was added with ice-cooling to 2-propenyloxyimino-2-(2-aminothiazole-4-yl)acetic acid (syn-isomer) (0.53 g) and the mixture was stirred for 20 minutes (B-solution).

To A-solution was added dropwise B-solution at −20° C. and the mixture was stirred at −10° C. to −20° C. for 1.5 hours. To the reaction mixture was added 30 ml of ice-water with cooling at −20° C. to −30° C., and further added 50 ml of ethyl acetate. The mixture was stirred and the insolubles were filtered off to obtain an organic layer. To the organic layer was added a saturated aqueous solution of sodium hydrogen carbonate to adjust a pH to 7.5. The separated aqueous layer was washed with methylene chloride. The aqueous layer was adjusted to pH 2 with 100% hydrochloric acid and precipitates were collected by filtration, dried and dissolved into 5% aqueous solution of potassium hydrogen carbonate. The solution was passed through Sephadex LH-20 (H$_2$O) to obtain 18 mg of the same compound as in Example 7, i.e., 7-[2-(2-aminothiazole-4-yl)-2-(2-propenoxyimino)acetamide]-3-[3-(2-propenyl)-1-imidazoliomethyl]-3-cephem-4-carboxylate (syn-isomer).

EXAMPLE 72

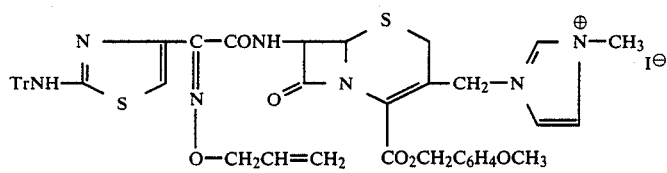

Into a solvent mixture of acetonitrile (5 ml) and chloroform (2.5 ml) was dissolved 230 mg of 7-[2-(2-propenyloxyimino)-2-(2-tritylaminothiazole-4-yl)acetamide]-3-(1-imidazoliomethyl)-3-cephem-1-oxide-4-carboxylic acid p-methoxybenzyl ester.iodide (syn-isomer) which was obtained by reducing with phosphorus tribromide the compound of Example 34 in the same manner as in Example 7. To the solution was added 0.5 ml of propylene oxide, 2 ml of methyl iodide and the mixture was stirred at room temperature for 18 hours. Solvents and excess of methyl iodide were removed at a reduced pressure to obtain 205 mg of 7-[2-(2-propenyloxyimino)-2-(2-tritylaminothiazole-4-yl)acetamide]-3-(3-methyl-1-imidazoliomethyl)-3-cephem-4-carboxylic acid p-methoxybenzyl ester.iodide (syn-isomer).

NMR $\delta$ ppm (DMSO-$d_6$): 3.65(2H,m), 3.73(3H,s), 3.85(3H,s), 4.64(2H,m), 4.97(1H,m), 5.0–5.50(6H,m), 5.6–6.40(2H,m), 6.92(1H,s), 7.07(4H,m), 7.31(15H,s), 7.60(2H,m), 8.80(1H,s).

EXAMPLE 73

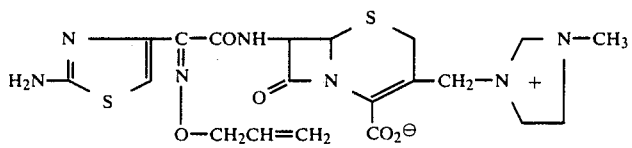

In the same manner as in Examples 6 and 7, from 200 mg of 7-[2-(2-propenyloxyimino)-2-(2-tritylamino-thiazole-4-yl)acetamide]-3-(3-methyl-1-imidazoliomethyl)-3-cephem-4-carboxylic acid p-methoxybenzyl ester.iodide (syn-isomer) was obtained 18 mg of 7-[2-(2-aminothiazole-4-yl)-2-(2-propenyloxyimino)acetamide]-3-(3-methyl-1-imidazoliomethyl)-3-cephem-4-carboxylate (syn-isomer).

NMR $\delta$ ppm (DMSO-$d_6$): 3.48(2H,m), 3.85(3H,s), 4.17(2H,s), 4.90–5.50(5H,m), 5.86(1H,m), 5.70–6.40(1H,m), 7.65(2H,s), 9.10(1H,s).

EXAMPLE 74

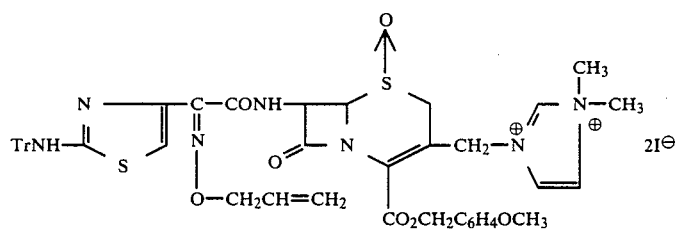

Into a solvent mixture of acetonitrile (3 ml) of chloroform (1.5 ml) was dissolved 400 mg of 7-[2-(2-propenyloxyimino)-2-(2-tritylaminothiazole-4-yl)acetamide]-3-(3-methyl-1-imidazoliomethyl)-3-cephem-1-oxide-4-carboxylic acid p-methoxybenzyl ester.iodide (syn-isomer) which was obtained in Example 26. To the solution was added 0.5 ml of propylene oxide, 0.78 ml of methyl iodide and the mixture was stirred at room temperature for 18 hours. Solvents and excess of methyl iodide were removed at a reduced pressure to obtain 363 mg of 7-[2-(2-propenyloxyimino)-2-(2-tritylaminothiazole-4-yl)acetamide]-3-(3,3-dimethyl-1-imidazoliomethyl)-3-cephem-1-oxide-4-carboxylic acid p-methoxybenzyl ester.diiodide (syn-isomer).

NMR $\delta$ ppm (DMSO-$d_6$): 3.65(2H,m), 3.73(3H,s), 3.85(6H,s), 4.64(2H,m), 4.97(1H,m), 5.0–5.50(6H,m), 5.6–6.40(2H,m), 6.92(1H,s), 7.07(4H,m), 7.31(15H,s), 7.60(2H,m), 8.80(1H,s).

EXAMPLE 75

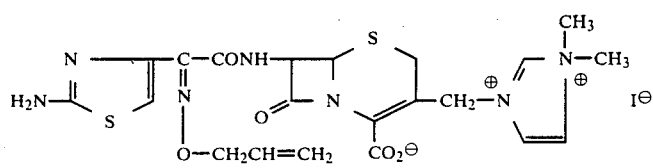

In the same manner as in Examples 5, 6 and 7, from 350 mg of 7-[2-(2-propenyloxyimino)-2-(2-tritylaminothiazole-4-yl)acetamide]-3-(3,3-dimethyl-1-imidazoliomethyl)-3-cephem-1-oxide-4-carboxylic acid p- methoxybenzyl ester.diiodide (syn-isomer) was obtained 18 mg of 7-[2-(2-aminothiazole-4-yl)-2-(2-propenyloxyimino)acetamide]-3-(3,3-dimethyl-1-imidazoliomethyl)-3-cephem-4-carboxylate.iodide (syn-isomer).

NMR δ ppm (DMSO-d$_6$): 3.48(2H,m), 3.85(6H,s), 4.17(2H,s), 4.90–5.50(5H,m), 5.86(1H,m), 5.70–6.40(1H,m), 7.65(2H,s), 9.10(1H,s).

EXAMPLE 76 boxylic acid p-methoxybenzyl ester.iodide (syn-isomer) was obtained 25.9 mg of 7-{2-(2-aminothiazole-4-yl)-2-[potassium(2,2-dimethylacetate)oxyimino]acetamide}-3-(3-vinyl-1-imidazoliomethyl)-3-cephem-4-carboxylate (syn-isomer).

NMR δ ppm (DMSO-d$_6$): 1.38(3H,s), 1.44(3H,s), 3.10–3.77(2H,m), 4.65–5.50(4H,m), 4.98(1H,d,J=5.0Hz), 5.64(1H,dd,J=5.0,8.0Hz), 6.75(1H,s), 6.90–7.60(1H,m), 7.12(1H,s), 7.98(1H,s), 8.11(1H,s), 9.70(1H,s), 12.06(1H,d,J=8.0Hz).

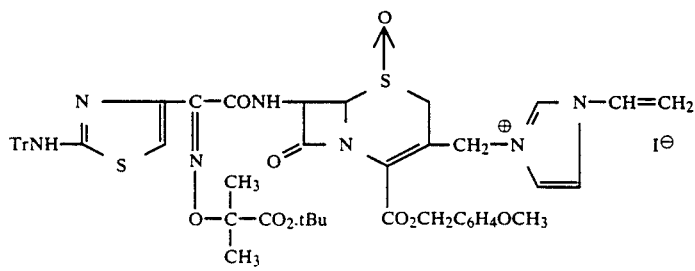

In the same manner as in Example 44, from 500 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 68 mg of 1-vinyl-imidazole was obtained 317.5 mg of 7-[2-(2-tert-butoxycarbonyl)prop-2-oxyimino-2-(2-tritylaminothiazole-4-yl)acetamide]-3-(3-vinyl-1-imidazoliomethyl)-3-cephem-1-oxido-4-carboxylic acid p-methoxybenzyl ester.iodide (syn-isomer).

NMR δ ppm (CDCl$_3$): 1.39(9H,s), 1.55(6H,s), 3.71(3H,s), 4.07(2H,m), 4.97(1H,d,J=5.0Hz), 4.75–5.91(4H,m), 5.21(2H,s), 6.10(1H,dd,J=5.0,8.0Hz), 6.72(1H,s), 7.05(4H,dd,J=8.0,35.0Hz), 6.61–8.09(5H,m), 7.25(15H,s), 9.68(1H,s).

EXAMPLE 77

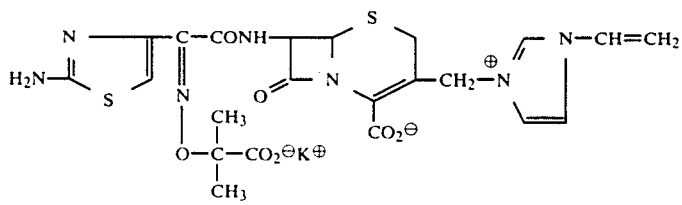

In the same manner as in Examples 45 and 46, from 300 mg of 7-[2-(2-tert-butoxycarbonyl)prop-2-oxyimino-2-(2-tritylaminothiazole-4-yl)acetamide]-3-(3-vinyl-1-imidazoliomethyl)-3-cephem-1-oxido-4-car-

EXAMPLE 78

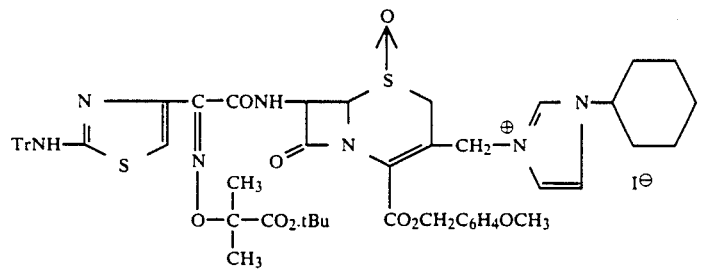

In the same manner as in Example 44, from 500 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 220 mg of 1-cyclohexylimidazole was obtained 185.8 mg of 7-[2-(2-tert-butoxycarbonyl)-prop-2-oxyimino-2-(2-tritylaminothiazole-4-yl)acetamide]-3-(3-cyclohexyl-1-imidazoliomethyl)-3-cephem-1-oxido-4-carboxylic acid p-methoxybenzyl ester.iodide (syn-isomer).

NMR δ ppm (CDCl$_3$): 1.35(9H,s), 1.50(6H,s), 0.95–2.30(11H,m), 3.73(3H,s), 4.08(2H,m), 4.92(1H,d,J=5.0Hz), 5.17(2H,s), 5.0–5.92(2H,m), 6.08(1H,dd,J=5.0,8.0Hz), 6.61(1H,s), 7.04(4H,dd,J=8.0,37.5Hz), 7.24(15H,s), 7.05–7.94(4H,m), 9.65(1H,s).

EXAMPLE 79

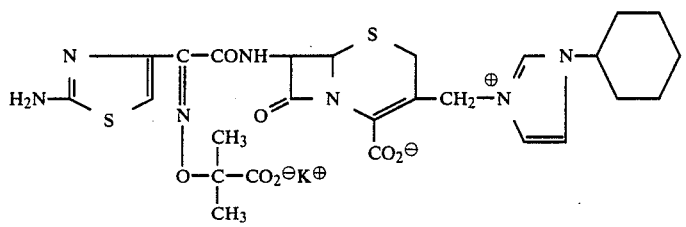

In the same manner as in Examples 45 and 46, from 185 mg of 7-[2-(2-tert-butoxycarbonyl)prop-2-oxyimino-2-(2-tritylaminothiazole-4-yl)acetamide]-3-(3-cyclohexyl-1-imidazoliomethyl)-3-cephem-1-oxido-4-carboxylic acid p-methoxybenzyl ester.iodide (syn-isomer) was obtained 8.8 mg of 7-{2-(2-aminothiazole-4-yl)-2-[potassium(2,2-dimethylacetate)oxyimino]acetamide}-3-(3-cyclohexyl-1-imidazoliomethyl)-3-cephem-4-carboxylate (syn-isomer).

NMR δ ppm (DMSO-$d_6$): 1.41(3H,s), 1.44(3H,s), 0.81-2.36(11H,m), 3.10-3.75(2H,m), 4.97(1H,d,J=5.0Hz), 5.05-5.45(2H,m), 5.50-5.85(1H,m), 6.69(1H,s), 7.10(2H,s), 7.58(1H,s), 8.00(1H,s), 9.46(1H,s), 12.13(1H,d,J=8.0Hz).

EXAMPLE 80

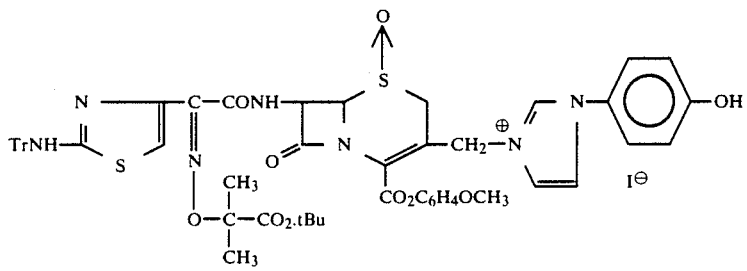

In the same manner as in Example 44, from 350 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 65 mg of 1-(4-hydroxyphenyl-)imidazole was obtained 160.9 mg of 7-[2-(2-tert-butoxycarbonyl)prop-2-oxyimino-2-(2-tritylaminothiazole-4-yl)acetamide]-3-[3-(4-hydroxyphenyl)-1-imidazoliomethyl]-3-cephem-1-oxido-4-carboxylic acid p-methoxybenzyl ester.iodide (syn-isomer).

NMR δ ppm (CDCl$_3$): 1.37(9H,s), 1.54(6H,s), 3.76(3H,s), 4.13(2H,m), 4.99(1H,d,J=5.0Hz), 5.24(2H,s), 5.05-5.85(2H,m), 6.14(1H,dd,J=5.0,8.0Hz), 6.63(1H,s), 7.07(4H,dd,J=8.0,37.5Hz), 6.65-8.10(9H,m), 7.23(15H,s), 9.71(1H,s).

EXAMPLE 81

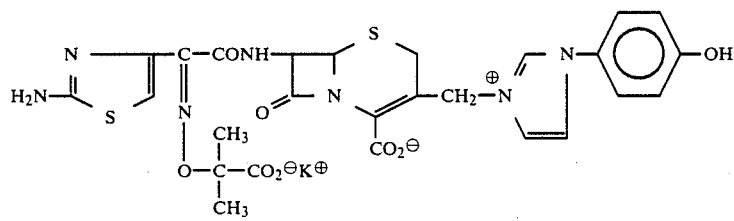

In the same manner as in Examples 45 and 46, from 160 mg of 7-[2-(2-tert-butoxycarbonyl)prop-2-oxyimino-2-(2-tritylaminothiazole-4-yl)acetamide]-3-[3-(4-hydroxyphenyl)-1-imidazoliomethyl]-3-cephem-1-oxido-4-carboxylic acid p-methoxybenzyl ester.iodide (syn-isomer) was obtained 9.0 mg of 7-{2-(2-aminothiazole-4-yl)-2-[potassium(2,2-dimethylacetate)oxyimino]acetamide}-3-[3-(4-hydroxyphenyl)-1-imidazoliomethyl]-3-cephem-4-carboxylate (syn-isomer).

NMR δ ppm (DMSO-$d_6$): 1.39(3H,s), 1.41(3H,s), 3.20-3.72(2H,m), 4.95(1H,d,J=5.0Hz), 5.05-5.40(2H,m), 5.47-5.84(1H,m), 6.72(1H,s), 6.23-8.25(9H,m), 9.47(1H,s), 12.03(1H,d,J=8.0Hz).

EXAMPLE 82

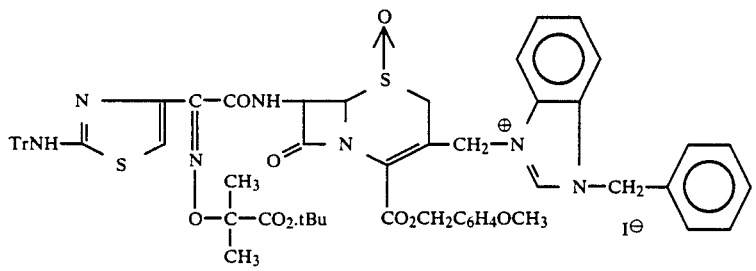

In the same manner as in Example 44, from 500 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 121 mg of 1-benzylbenzimidazole was obtained 288.5 mg of 7-[2-(2-tert-butoxycarbonyl)-prop-2-oxyimino-2-(2-tritylaminothiazole-4-yl)acetamide]-3-(benz-3-N-benzyl-1-imidazoliomethyl)-3-cephem-1-oxido-4-carboxylic acid p-methoxybenzyl ester.iodide (syn-isomer).

NMR δ ppm (CDCl$_3$): 1.39(9H,s), 1.54(6H,s), 3.74(3H,s), 4.16(2H,m), 5.13(1H,d,J=5.0Hz), 5.23(2H,s), 6.10(2H,s), 5.75(2H,m), 6.11(1H,dd,J=5.0,8.0Hz), 7.02(4H,dd,J=8.0,42.5Hz), 7.25(15H,s), 7.37(5H,s), 6.70–8.10(7H,m).

EXAMPLE 83

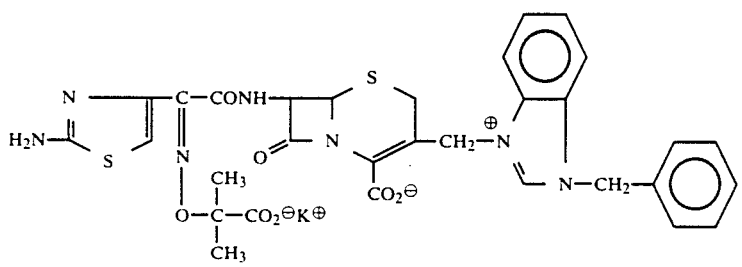

In the same manner as in Examples 45 and 46, from 280 mg of 7-[2-(2-tert-butoxycarbonyl)prop-2-oxyimino-2-(2-tritylaminothiazole-4-yl)acetamide]-3-(benz-3-N-benzyl-1-imidazoliomethyl)-3-cephem-1-oxido-4-carboxylic acid p-methoxybenzyl ester.iodide (syn-isomer) was obtained 30.1 mg of 7-{2-(2-amino-thiazole-4-yl)-2-[potassium(2,2-dimethylacetate)ox-yimino]acetamide}-3-(benz-3-N-benzyl-1-imidazoliomethyl)-3-cephem-4-carboxylate (syn-isomer).

NMR δ ppm (DMSO-d$_6$): 1.35(3H,s), 1.40(3H,s), 3.08–3.76(2H,m), 4.93(1H,d,J=5.0Hz), 5.45(2H,s), 5.77(2H,s), 5.46–5.82(1H,m), 6.66(1H,s), 6.85–8.50(9H,m), 7.07(2H,s), 10.13(1H,s), 11.84(1H,d,J=8.0Hz).

EXAMPLE 84

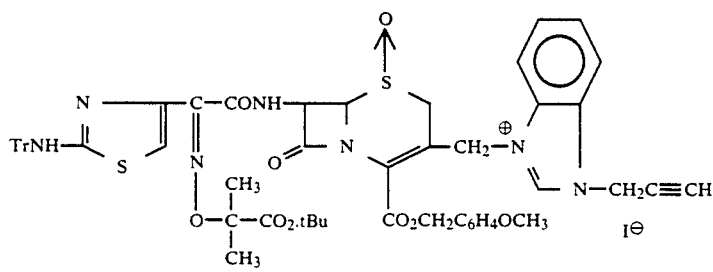

In the same manner as in Example 44, from 350 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 64 mg of 1-(2-propynyl)benzimidazole was obtained 209.1 mg of 7-[2-(2-tert-butoxycarbonyl)prop-2-oxyimino-2-(2-tritylaminothiazole-4-yl)acetamide]-3-[benz-3-N-(2-propynyl)-1-imidazoliomethyl]-3-cephem-1-oxido-4-carboxylic acid p-methoxybenzyl ester.iodide (syn-isomer).

NMR δ ppm (CDCl$_3$): 1.38(9H,s), 1.52(6H,s), 2.47(1H,t,J=2.8Hz), 3.72(3H,s), 4.07(2H,m), 4.88(2H,d,J=2.8Hz), 5.16(1H,d,J=5.0Hz), 5.25(2H,s), 6.03(2H,m), 6.23(1H,dd,J=5.0,8.0Hz), 6.59(1H,s), 7.01(4H,dd,J=8.0,42.5Hz), 7.26(15H,s), 6.62–8.10(6H,m), 10.31(1H,s).

EXAMPLE 85

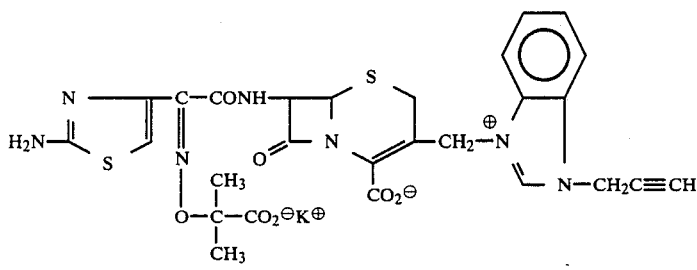

In the same manner as in Examples 45 and 46, from 217.6 mg of 7-[2-(2-tert-butoxycarbonyl)prop-2-oxyimino-2-(2-tritylaminothiazole-4-yl)acetamide]-3-[benz-3-N-(2-propynyl)-1-imidazoliomethyl]-3-cephem-1-oxido-4-carboxylic acid p-methoxybenzyl ester.iodide (syn-isomer) was obtained 36.5 mg of 7-{2-(2-aminothiazole-4-yl)-2-[potassium(2,2-dimethylacetate)oxyimino]acetamide}-3-[benz-3-N-(2-propynyl)-1-imidazoliomethyl]-3-cephem-4-carboxylate (syn-isomer).

NMR δ ppm (DMSO-$d_6$): 1.38(3H,s), 1.42(3H,s), 3.35–3.86(2H,m), 4.96(1H,d,J=5.0Hz), 5.05–5.82(5H,m,), 6.67(1H,s), 7.10(2H,s), 6.96–8.50(4H,m), 10.06(1H,s), 11.17(1H,d,J=8.0Hz).

EXAMPLE 86

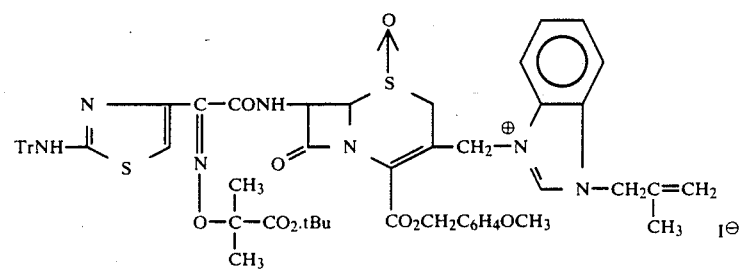

In the same manner as in Example 44, from 500 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 100 mg of 1-(2-methyl-2-propenyl)benzimidazole was obtained 268.9 mg of 7-[2--(2-tert-butoxycarbonyl)prop-2-oxyimino-2-(2-tritylaminothiazole-4-yl)acetamide]-3-[benz-3-N-(2-methyl-2-propenyl)-1-imidazoliomethyl]-3-cephem-1-oxido-4-carboxylic acid p-methoxybenzyl ester.iodide (syn-isomer).

NMR δ ppm (CDCl$_3$): 1.40(9H,s), 1.54(6H,s), 1.75(3H,s), 4.17(2H,m), 4.66(2H,s), 4.85–5.40(3H,m), 5.21(2H,s), 5.75(2H,m), 6.20(1H,dd,J=5.0,8.0Hz), 6.59(1H,s), 7.02(4H,dd,J=8.0,42.5Hz), 7.25(15H,s), 6.70–8.15(7H,m).

EXAMPLE 87

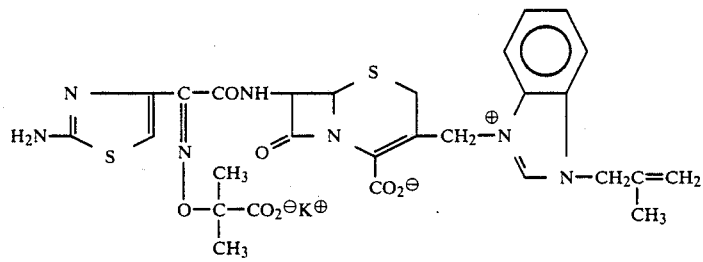

In the same manner as in Examples 45 and 46, from 265 mg of 7-[2-(2-tert-butoxycarbonyl)prop-2-oxyimino-2-(2-tritylaminothiazole-4-yl)acetamide]-3-[benz-3-N-(2-methyl-2-propenyl-1-imidazoliomethyl]-3-cephem-1-oxido-4-carboxylic was obtained 30.8 mg of 7-{2-(2-aminothiazole-4-yl)-2-[potassium(2,2-dimethylacetate)oxyimino]acetamide}-3-[benz-3-N-(2-methyl-2-propenyl)-1-imidazoliomethyl]-3-cephem-4-carboxylate (syn-isomer).

NMR δ ppm (DMSO-$d_6$): 1.37(3H,s), 1.42(3H,s), 2.24(3H,s), 3.32–3.75(2H,m), 4.55–5.25(2H,m), 4.95(1H,d,J=5.0Hz), 5.15(2H,s), 5.42(2H,s), 5.62(1H,dd,J=5.0,8.0Hz), 6.67(1H,s), 7.07(2H,s), 6.81–8.46(4H,m), 9.99(1H,s), 11.58(1H,d,J=8.0Hz).

EXAMPLE 88

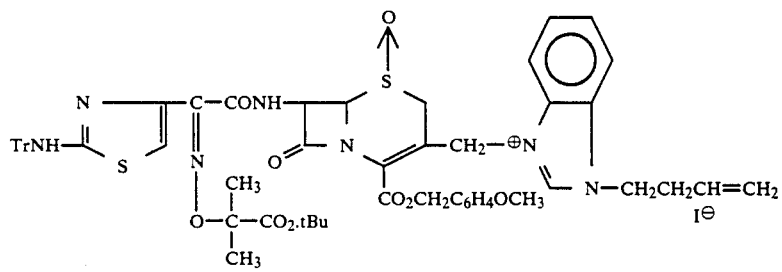

In the same manner as in Example 44, from 350 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 70 mg of 1-(3-butenyl)benzimidazole was obtained 214 mg of 7-[2-(2-tert-butoxycarbonyl)prop-2-oxyimino-2-(2-tritylaminothiazole-4-yl)acetamide]-3-[benz-3-N-(3-butenyl)-1-imidazoliomethyl]-3-cephem-1-oxido-4-carboxylic acid p-methoxybenzyl ester.iodide (syn-isomer).

NMR δ ppm (CDCl$_3$): 1.38(9H,s), 1.52(6H,s), 2.72(2H,q,J=6.0Hz), 3.80(3H,s), 4.14(2H,m), 4.48(2H,t,J=6.0Hz), 5.20(2H,s), 4.80–5.26(3H,m), 5.67(2H,m), 5.70–6.20(1H,m), 6.17(1H,dd,J=5.0,8.0Hz), 6.58(1H,s), 7.02(4H,dd,J=8.0,42.5Hz), 7.24(15H,s), 6.75–8.08(6H,m), 10.6(1H,s).

EXAMPLE 89

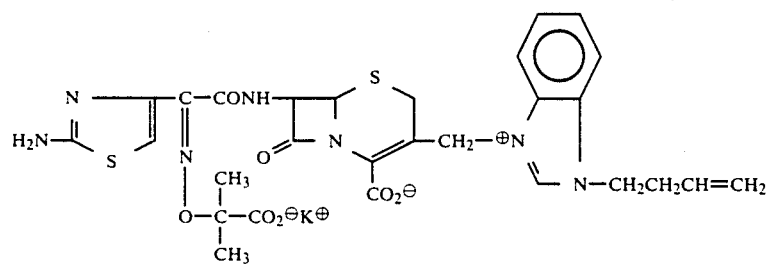

In the same manner as in Examples 45 and 46, from 210 mg of 7-[2-(2-tert-butoxycarbonyl)prop-2-oxyimino-2-(2-tritylaminothiazole-4-yl)acetamide]-3-[benz-3-N-(3-butenyl)-1-imidazoliomethyl]-3-cephem-1-oxido-4-carboxylic acid p-methoxybenzyl ester.iodide (syn-isomer) was obtained 25.3 mg of 7-{2-(2-aminothiazole-4-yl)-2-[potassium(2,2-dimethylacetate)oxyimino]acetamide}-3-[benz-3-N-(3-butenyl)-1-imidazoliomethyl]-3-cephem-4-carboxylate (syn-isomer).

NMR δ ppm (DMSO-d$_6$): 1.36(3H,s), 1.41(3H,s), 2.66(2H,q,J=6.0Hz), 3.30–3.75(2H,m), 4.58(2H,t,J=6.0Hz), 4.92(1H,d,J=5.0Hz), 5.04(2H,s), 5.25–6.22(4H,m), 6.67(1H,s), 7.07(2H,s), 7.35–8.47(4H,m), 10.3(1H,s), 11.91(1H,d,J=8.0Hz).

EXAMPLE 90

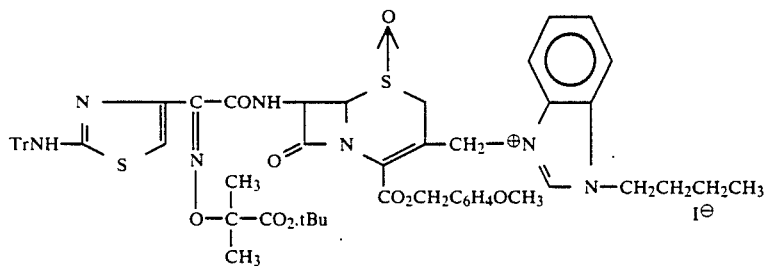

In the same manner as in Example 44, from 350 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 71 mg of 1-butylbenzimidazole was obtained 198 mg of 7-[2-(2-tert-butoxycarbonyl)prop-2-oxyimino-2-(2-tritylaminothiazole-4-yl)acetamide]-3-(benz-3-N-buty-1-imidazoliomethyl)-3-cephem-1-oxido-4-carboxylic acid p-methoxybenzyl ester.iodide (syn-isomer).

NMR δ ppm (CDCl$_3$): 0.97(3H,t,J=6.0Hz), 1.48(9H,s), 1.52(6H,s), 1.70–2.25(4H,m), 3.75(3H,s), 4.18(2H,m), 4.40(2H,t,J=6.0Hz), 5.16(1H,d,J=5.0Hz), 5.22(2H,s), 5.72(2H,m), 6.17(1H,dd,J=5.0,8.0Hz), 6.58(1H,s), 7.02(4H,dd,J=8.0,42.5Hz), 7.24(15H,s), 6.65–8.20(7H,m).

EXAMPLE 91

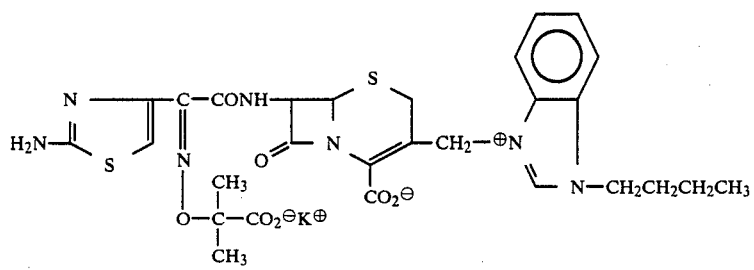

In the same manner as in Examples 45 and 46, from 195 mg of 7-[2-(2-tert-butoxycarbonyl)prop-2-oxyimino-2-(2-tritylaminothiazole-4-yl)acetamide]-3-(benz-3-N-butyl-1-imidazoliomethyl)-3-cephem-1-oxido-4-carboxylic acid p-methoxybenzyl ester.iodide (syn-isomer) was obtained 24.0 mg of 7-{2-(2-aminothiazole-4-yl)-2-[potassium(2,2-dimethylacetate)oxyimino]acetamide}-3-(benz-3-N-butyl-1-imidazoliomethyl)-3-cephem-4-carboxylate (syn-isomer).

NMR δppm (DMSO-$d_6$): 0.92(3H,t,J=6.0Hz), 1.37(3H,s), 1.41(3H,s), 1.27(2H,m), 1.83(2H,m), 3.15–3.75(2H,m), 4.48(2H,t,J=6.0Hz), 4.93(1H,d,J=5.0Hz), 5.42(2H,s), 5.30–5.83(1H,m), 6.67(1H,s), 6.95–8.48(4H,m), 7.07(2H,s), 10.00(1H,s), 11.83(1H,d,J=8.0Hz).

EXAMPLE 92

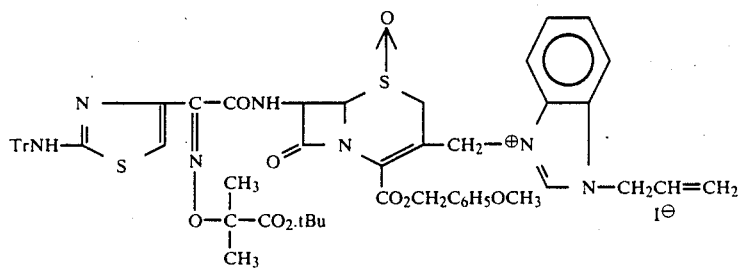

In the same manner as in Example 44, from 350 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 65 mg of 1-(2-propenyl)benzimidazole was obtained 224.3 mg of 7-[2-(2-tert-butoxycarbonyl)prop-2-oxyimino-2-(2-tritylaminothiazole-4-yl)acetamide]-3-[benz-3-N-(2-propenyl)-1-imidazoliomethyl]-3-cephem-1-oxido-4-carboxylic acid p-methoxybenzyl ester.iodide (syn-isomer).

NMR δ ppm (CDCl$_3$): 1.40(9H,s), 1.54(6H,s), 3.66(3H,s), 4.11(2H,m), 4.76(2H,d,J=6.3Hz), 5.02(1H,d,J=5.0Hz), 5.23(2H,s), 5.05–6.14(2H,m), 6.37–6.70(4H,m), 6.61(1H,s), 7.04(4H,dd,J=8.0,42.5Hz), 7.26(15H,s), 6.65–8.15(7H,m).

EXAMPLE 93

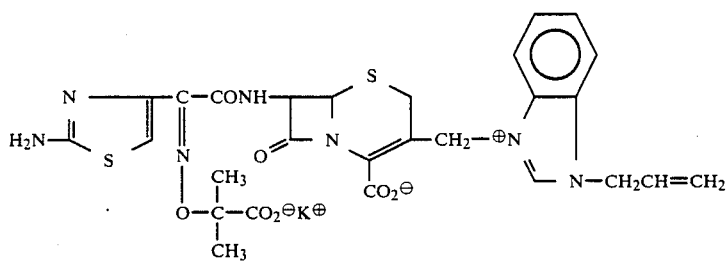

In the same manner as in Examples 45 and 46, from 200 mg of 7-[2-(2-tert-butoxycarbonyl)prop-2-oxyimino-2-(2-tritylaminothiazole-4-yl)acetamide]-3-[benz-3-N-(2-propenyl)-1-imidazoliomethyl]-3-cephem-1-oxido-4-carboxylic acid p-methoxybenzyl ester.iodide (syn-isomer) was obtained 11.5 mg of 7-{2-(2-aminothiazole-4-yl)-2-[potassium(2,2-dimethylacetate)oxyimino]acetamide}-3-[benz-3-N-(2-propenyl)-1-imidazoliomethyl]-3-cephem-4-carboxylate (syn-isomer).

NMR δ ppm (DMSO-$d_6$): 1.37(3H,s), 1.39(3H,s), 3.12–3.77(2H,m), 4.87(2H,d,J=6.0Hz), 4.93(1H,d,J=5.0Hz), 5.02–5.74(3H,m), 5.40(2H,s), 5.74–6.34(1H,m), 6.65(1H,s), 6.41–8.46(4H,m), 7.10(2H,s), 9.91(1H,s), 11.90(1H,d,J=8.0Hz).

EXAMPLE 94

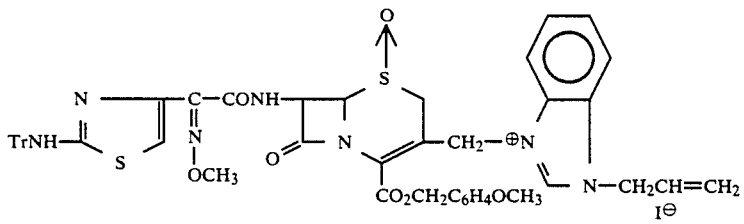

In the same manner as in Example 4, from 450 mg of 7-[2-methoxyimino-2-(2-tritylaminothiazole-4-yl)acetamide]-3-iodomethyl-3-cephem-1-oxido-4-carboxylic acid p-methoxybenzyl ester (syn-isomer) and 87 mg of 1-(2-propenyl)benzimidazole was obtained 130 mg of 7-[2-methoxyimino-2-(2-tritylaminothiazole-4-yl)-acetamide]-3-[benz-3-N-(2-propenyl)-1-imidazoliomethyl]-3-cephem-1-oxido-4-carboxylic acid p-methoxybenzyl ester.iodide (syn-isomer).

NMR δ ppm (DMSO-$d_6$): 3.75(3H,s), 3.80(3H,s), 4.1–4.3(2H,m), 4.45(2H,s), 4.90–5.10(2H,m), 5.22(4H,s), 5.45(2H,s), 5.5–5.65(1H,m), 6.75(1H;s), 7.25(15H,s), 9.20(1H,s).

EXAMPLE 95

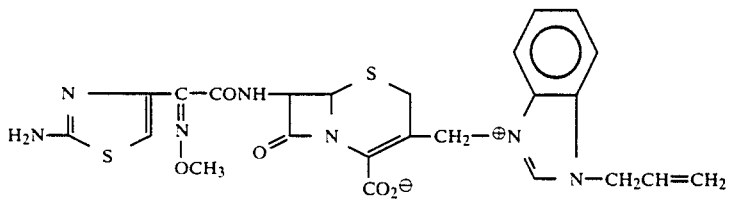

In the same manner as in Examples 5, 6 and 7, from 120 mg of 7-[2-methoxyimino-2-(2-tritylaminothiazole-4-yl)acetamide]-3-[benz-3-N-(2-propenyl)-1-imidazoliomethyl]-3-cephem-1-oxido-4-carboxylic acid p-methoxybenzyl ester.iodide (syn-isomer) was obtained 17 mg of 7-[2-(2-aminothiazole-4-yl)-2-methoxyiminoacetamide}-3-[benz-3-N-(2-propenyl)-1-imidazoliomethyl]-3-cephem-4-carboxylate (syn-isomer).

NMR δ ppm (DMSO-$d_6$): 3.10–3.70(2H,m), 3.80(3H,s), 4.1–4.3(2H,m), 4.40–4.50(2H,m), 4.98(2H,d,J=8.0Hz), 5.22–5.45(4H,m), 6.75(1H,s), 12.5(1H,d,J=8.0Hz).

EXAMPLE 96

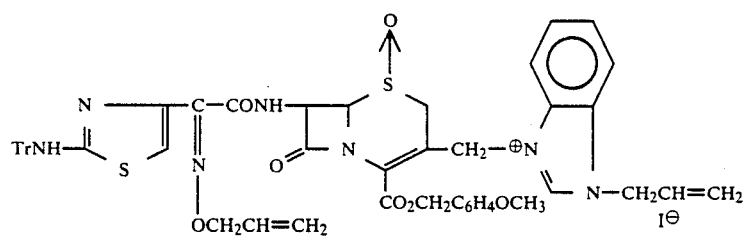

In the same manner as in Example 4, from 460 mg of 7-[2-(2-propenyloxyimino)-2-(2-tritylaminothiazole-4-yl)acetamide]-3-iodomethyl-3-cephem-1-oxido-4-carboxylic acid p-methoxybenzyl ester (syn-isomer) and 87 mg of 1-(2-propenyl)benzimidazole was obtained 140 mg of 7-[2-(2-propenyloxyimino)-2-(2-tritylaminothiazole-4-yl)acetamide]-3-[benz-3-N-(2-propenyl)-1-imidazoliomethyl]-3-cephem-1-oxido-4-carboxylic acid p-methoxybenzyl ester.iodide (syn-isomer).

NMR δ ppm (DMSO-$d_6$): 3.75(3H,s), 4.2–4.3(4H,m), 4.45(2H,s), 5.05–5.15(4H,m), 5.22–5.45(6H,m), 5.5–5.6(2H,m), 6.75(1H,s), 7.08–7.15(4H,m), 7.25(15H,s), 9.20(1H,s).

EXAMPLE 97

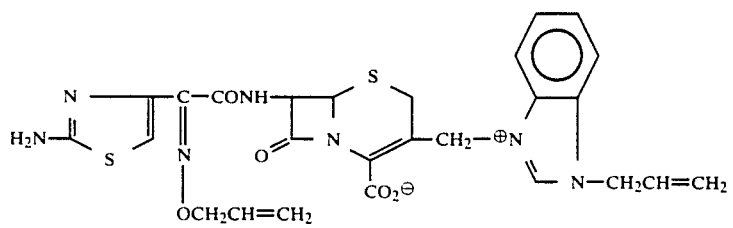

In the same manner as in Examples 5, 6 and 7, from 130 mg of 7-[2-(2-propenyloxyimino)-2-(2-tritylaminothiazole-4-yl)acetamide]-3-[benz-3-N-(2-propenyl)-1-imidazoliomethyl]-3-cephem-1-oxido-4-carboxylic acid p-methoxybenzyl ester.iodide (syn-isomer) was obtained 26 mg of 7-[2-(2-aminothiazole-4-yl)-2-(2-propenyloxyimino)acetamide]-3-[benz-3-N-(2-propenyl)-1-imidazoliomethyl]-3-cephem-4-carboxylate (syn-isomer).

NMR δ ppm (DMSO-$d_6$): 3.60–3.65(2H,m), 4.2–4.3(4H,m), 4.45(2H,s), 5.05–5.15(4H,m), 5.22–5.45(4H,m), 5.5–5.6(2H,m), 6.75(1H,s), 12.5(1H,d,J=8.0Hz).

EXAMPLE 98

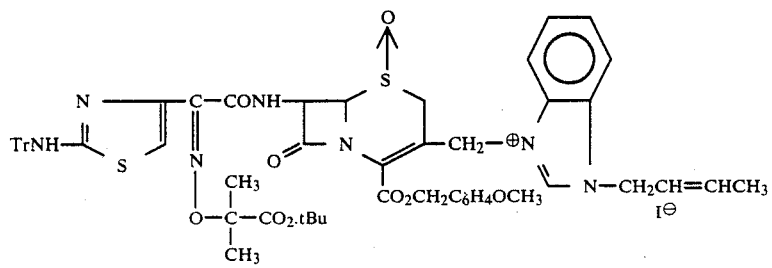

In the same manner as in Example 44, from 502 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 103 mg of 1-(2-butenyl)benzimidazole was obtained 410 mg of 7-[2-(2-tert-butoxycarbonyl)prop-2-oxyimino-2-(2-tritylaminothiazole-4-yl)acetamide]-3-[benz-3-N-(2-butenyl)-1-imidazoliomethyl]-3-cephem-1-oxido-4carboxylic acid p-methoxybenzyl ester.iodide (syn-isomer).

NMR δ ppm (DMSO-$d_6$): 1.34(9H,s), 1.44(3H,s), 1.7(3H,s), 4.7–4.85(3H,m), 5.30(2H,s), 5.5–5.9(3H,m), 6.60(1H,s), 7.25(15H,s), 9.20(1H,s).

EXAMPLE 99

[benz-3-N-(2-butenyl)-1-imidazoliomethyl]-3-cephem-1-oxido-4-carboxylic acid p-methoxybenzyl ester.iodide (syn-isomer) was obtained 21.5 mg of 7-{2-(2-aminothiazole-4-yl)-2-[potassium(2,2-dimethylacetate)oxyimino]acetamide}-3-[benz-3-N-(2-butenyl)-1-imidazoliomethyl]-3-cephem-4-carboxylate (syn-isomer).

NMR δ ppm (DMSO-$d_6$): 1.38(3H,s), 1.41(3H,s), 1.7(3H,s), 4.7–4.85(3H,m), 5.30(2H,s), 5.5–5.9(3H,m), 6.60(1H,s), 9.80(1H,s), 12.50(1H,d,J=8.0Hz).

EXAMPLE 100

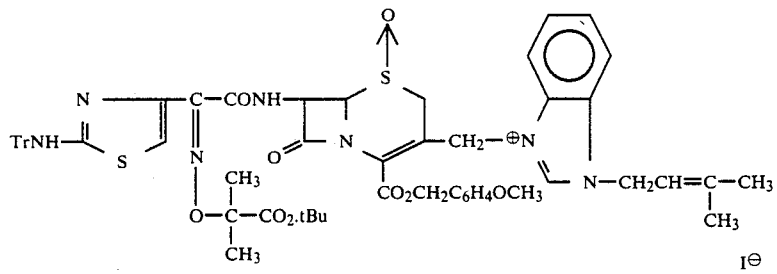

In the same manner as in Example 44, from 502 mg of 7-[2-(2-tert-butoxycarbonyl)prop-2-oxyimino-2-(2-tritylaminothiazole-4-yl)acetamide]-3-iodomethyl-3-cephem-1-oxido-4-carboxylic acid p-methoxybenzyl ester (syn-isomer) and 111 mg of 1-(3-methyl-2-butenyl)benzimidazole was obtained 380 mg of 7-[2-(-2-tert-butoxycarbonyl)prop-2-oxyimino-2-(2-tritylaminothiazole-4-yl)acetamide]-3-[benz-3-N-(3-methyl-2-butenyl)-1-imidazoliomethyl]-3-cephem-1-oxido-4-carboxylic acid p-methoxybenzyl ester.iodide (syn-isomer).

NMR δ ppm (DMSO-$d_6$): 1.34(9H,s), 1.39(6H,s), 1.80(6H,s), 4.7–4.85(3H,m), 5.30(2H,s), 5.3–5.6(2H,m), 6.60(1H,s), 7.25(15H,s), 9.20(1H,s).

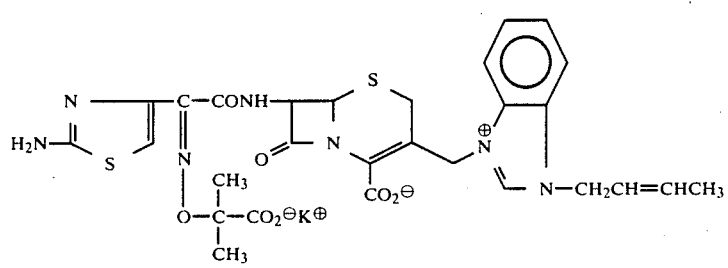

In the same manner as in Examples 45 and 46, from 280 mg of 7-[2-(2-tert-butoxycarbonyl)prop-2-oxyimino-2-(2-tritylaminothiazole-4-yl)acetamide]-3-

EXAMPLE 101

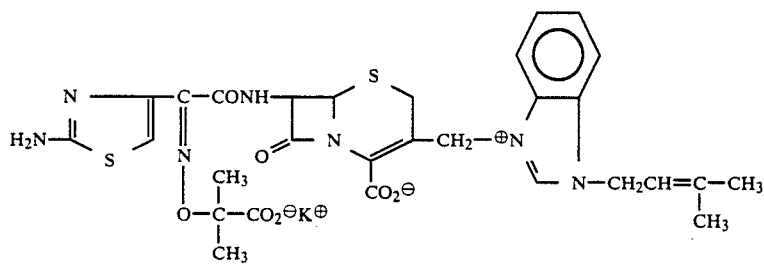

In the same manner as in Examples 45 and 46, from 260 mg of 7-[2-(2-tert-butoxycarbonyl)prop-2-oxyimino-2-(2-tritylaminothiazole-4-yl)acetamide]-3-[benz-3-N-(3-methyl-2-butenyl)-1-imidazoliomethyl]-3-cephem-1-oxido-4-carboxylic acid p-methoxybenzyl ester.iodide (syn-isomer) was obtained 12.6 mg of 7-{2-(2-aminothiazole-4-yl)-2-[potassium(2,2-dimethylacetate)oxyimino]acetamide}-3-[benz-3-N-(3-methyl-2-butenyl)-1-imidazoliomethyl]-3-cephem-4-carboxylate (syn-isomer).

NMR δ ppm (DMSO-$d_6$): 1.38(6H,s), 1.80(6H,s), 4.7–4.85(3H,m), 5.30(2H,s), 5.3–5.6(2H,m), 6.60(1H,s), 9.80(1H,s), 12.50(1H,d,J=8.0Hz).

EXAMPLE 102

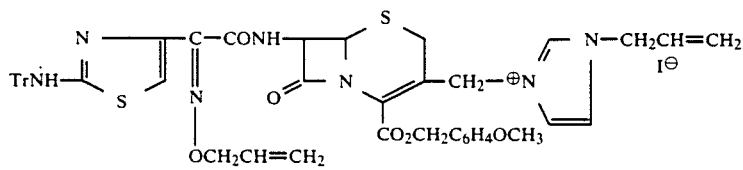

Into a solvent mixture of chloroform (600 ml) and acetonitrile (1000 ml) was dissolved 214.4 g of 7-[2-(2-propenyloxyimino)-2-(2-tritylaminothiazole-4-yl)acetamide]-3-iodomethyl-3-cephem-4-carboxylic acid p-methoxybenzyl ester (syn-isomer) obtained in Example 2. To the solution was added with ice-cooling 41.1 g of 1-(2-propenyl)imidazole. After the addition, the mixture was heated to room temperature and was further stirred for 4 hours. Solvents were removed at a reduced pressure. The residue was purified by a silica-gel column (chloroform/methanol=3/1, volume ratio) to collect eluate containing a desired compound. By removing a solvent was obtained 268 g of 7-[2-(2-propenyloxyimino)-2-(2-tritylaminothiazole-4-yl)acetamide]-3-[3-(2-propenyl)-1-imidazoliomethyl]-3-cephem-4-carboxylic acid p-methoxybenzyl ester.iodide (syn-isomer).

NMR δ ppm (DMSO-$d_6$): 3.55(2H,s), 3.77(3H,s), 4.58(2H,d,J=5.0Hz), 4.87(2H,d,J=5.0Hz), 4.98–5.60(9H,m), 5.62–6.35(3H,m), 6.76(1H,s), 7.12(4H,dd,J=8.0Hz,32.5Hz), 7.32(15H,s), 7.68(1H,s), 7.75(1H,s), 9.28(1H,s), 9.27(1H,s), 9.58(1H,d,J=8.0Hz).

In the order to demonstrate use of Compound (I) of the invention, typical compounds of the formula (I) were tested for in vitro anti-bacterial activity. The results were shown below.

TEST: IN VITRO ANTI-BACTERIAL ACTIVITY

Compounds tested:

A: Compound of Example 7
B: Compound of Example 15
C: Compound of Example 17
D: Compound of Example 19
E: Compound of Example 73
F: Compound of Example 33
G: Compound of Example 37
H: Compound of Example 46
I: Compound of Example 48
J: Compound of Example 52
K: Compound of Example 56
L: Compound of Example 64
M: Compound of Example 77
N: Compound of Example 79
O: Compound of Example 81

P: Compound of Example 83
Q: Compound of Example 85
R: Compound of Example 87
S: Compound of Example 89
T: Compound of Example 91
U: Compound of Example 93
V: Compound of Example 95
W: Compound of Example 97
X: Compound of Example 99
Y: Compound of Example 101

TEST METHOD

The agent for preventing and treating bacterial infections was tested for in vitro anti-bacterial activity by the following two-fold agar plate dilution method. Each test strain was incubated for 20 hours in a bouillon for measuring sensitivity to obtain a test culture (containing about 10% live cells/ml). Portions of sensitivity measuring agar medium containing varying concentrations of the antibacterial agent were each innoculated with a 0.005 ml portion of the culture, followed by incubation at 37° C. for 20 hours. The minimum growth inhibitory concentration (MIC) in μg/ml was then determined. Table 1 shows the result.

MIC=minimum inhibitory concentration

TABLE 1

| Compound | A | B | C | D | E | F |
|---|---|---|---|---|---|---|
| | | | | | MIC (μg/ml) | |
| *Staphylococcus aureus* 209P | 0.78 | 0.20 | 0.39 | 0.78 | 0.78 | 6.25 |
| *Escherichia coli* NIHJ-JC2 | 0.78 | 0.39 | 0.39 | 0.78 | 0.20 | 0.1 |
| *Klebsiella pneumoniae* | 1.56 | 0.39 | 0.78 | 0.78 | 0.02 | 0.1 |
| *Proteus vulgaris* | 1.56 | 0.78 | 0.78 | 1.56 | 0.39 | 0.39 |
| *Proteus mirabilis* | 3.13 | 0.78 | 0.78 | 1.56 | 0.78 | 0.39 |
| *Serratia marcescens* | 0.78 | 1.56 | 3.12 | 3.13 | 1.56 | 0.78 |
| *Escherichia coli* CSH(RE45) | 0.39 | 0.10 | 0.20 | 0.78 | 0.05 | 0.2 |
| *Pseudomonas aeruginosa* | 6.25 | 6.25 | 12.5 | 12.5 | 12.5 | 25 |
| *Pseudomonas cepacia* | 6.25 | 1.56 | 6.25 | 12.5 | >50 | 50 |

| Compound | G | H | I | J | K | L |
|---|---|---|---|---|---|---|
| *Staphylococcus aureus* 209P | 0.78 | 5.0 | 6.25 | 6.25 | 12.5 | 1.56 |
| *Escherichia coli* NIHJ-JC2 | 0.05 | 0.20 | 0.39 | 0.78 | 0.2 | 0.20 |
| *Klebsiella pneumoniae* | 0.1 | 0.78 | 1.56 | 1.56 | 0.78 | 0.78 |
| *Proteus vulgaris* | 0.2 | 0.10 | 0.2 | 0.20 | 0.39 | 0.20 |
| *Proteus mirabilis* | 0.2 | 0.20 | 0.2 | 0.39 | 0.39 | 0.20 |
| *Serratia marcescens* | 1.56 | 0.78 | 1.56 | 0.78 | 0.78 | 0.78 |
| *Escherichia coli* CSH(RE45) | 0.2 | 0.10 | 0.2 | 0.20 | 0.39 | 0.2 |
| *Pseudomonas aeruginosa* | 6.25 | 3.12 | 12.5 | 3.12 | 3.13 | 3.13 |
| *Pseudomonas cepacia* | 25 | 6.25 | 25 | 6.25 | 0.39 | 6.25 |

| Compound | M | N | O | P | Q | R |
|---|---|---|---|---|---|---|
| *Staphylococcus aureus* 209P | 6.25 | 6.25 | 6.25 | 3.13 | 3.13 | 6.25 |
| *Escherichia coli* NIHJ-JC2 | 0.2 | 0.2 | 0.2 | 3.13 | 0.2 | 0.78 |
| *Klebsiella pneumoniae* | 0.39 | 0.78 | 0.78 | 6.25 | 0.78 | 3.13 |
| *Proteus vulgaris* | 0.1 | 0.2 | 0.1 | 1.56 | 0.1 | 0.78 |
| *Proteus mirabilis* | 0.1 | 0.2 | 0.2 | 3.13 | 0.39 | 3.13 |
| *Serratia marcescens* | 0.78 | 1.56 | 0.78 | 6.25 | 0.78 | 1.56 |
| *Escherichia coli* CSH(RE45) | 0.1 | 0.1 | 0.1 | 1.56 | 0.2 | 1.56 |
| *Pseudomonas aeruginosa* | 3.13 | 6.25 | 6.25 | 6.25 | 3.13 | 12.5 |
| *Pseudomonas cepacia* | 12.5 | 25 | 25 | 50 | 12.5 | 25 |

| Compound | S | T | U | V | W | X | Y |
|---|---|---|---|---|---|---|---|
| *Staphylococcus aureus* 209P | 0.78 | 3.13 | 6.25 | 3.13 | 1.56 | 6.25 | 6.25 |
| *Escherichia coli* NIHJ-JC2 | 0.78 | 1.56 | 0.39 | 0.78 | 3.13 | 1.56 | 6.25 |
| *Klebsiella pneumoniae* | 3.13 | 3.13 | 0.78 | 1.56 | 6.25 | 3.13 | 12.5 |
| *Proteus vulgaris* | 0.78 | 0.78 | 0.39 | 3.13 | 3.13 | 1.56 | 3.13 |
| *Proteus mirabilis* | 3.13 | 3.13 | 1.56 | 6.25 | 6.25 | 1.56 | 6.25 |
| *Serratia marcesens* | 3.13 | 1.56 | 1.56 | 12.5 | 25 | 1.56 | 12.5 |
| *Escherichia coli* CSH(RE45) | 0.39 | 0.39 | 0.2 | 3.13 | 1.56 | 0.78 | 1.56 |
| *Pseudomonas aeruginosa* | 6.25 | 6.25 | 6.25 | >100 | 50 | 12.5 | 25 |
| *Pseudomonas cepacia* | 25 | 25 | 25 | >100 | >100 | 50 | >100 |

We claim:

1. A cephalosporin compound substituted by an imidazolium ring in 3-position of cephem having the formula (I) or (II)

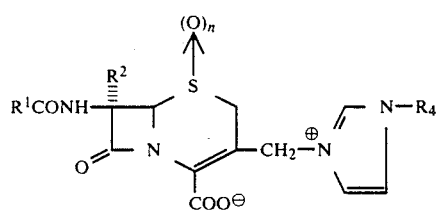
(I)

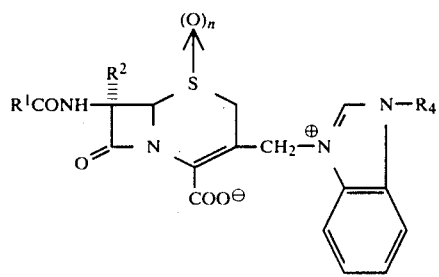
(II)

wherein R¹ is

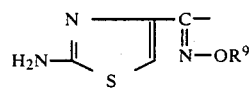

wherein $R^9$ is $C_2$-$C_6$ alkenyl or $C_2$-$C_6$ alkynyl; $R^2$ is hydrogen or methoxy; $R^4$ is $C_2$-$C_{12}$ alkenyl or $C_2$-$C_{12}$ alkynyl; and n is 0 to 1.

2. A compound according to claim 1, wherein $R^2$ is hydrogen and n is 0.

3. A compound according to claim 2, wherein $R^9$ is —$CH_2CH$=$CH_2$ or —$CH_2C$≡$CH$ 4. A compound according to claim 2, wherein $R_4$ is —$CH_2CH$=$CH_2$, —$CH_2C$≡$CH$ or —$CH$=$CH_2$.

5. A pharmaceutical composition for preventing and treating bacterial infections, said composition comprising an anti-bacterially effective amount of a cephalosporin compound of claim 1 or a pharmaceutically acceptable salt thereof in association with a pharmaceutically acceptable carrier.

6. A method of preventing or treating bacterial infections in a patient in need of such therapy, said method comprising administering to said patient an anti-bacterially effective amount of a cephalosporin compound of claim 1.

* * * * *